(12) United States Patent
Herlyn et al.

(10) Patent No.: US 7,544,465 B2
(45) Date of Patent: Jun. 9, 2009

(54) METHODS AND COMPOSITIONS FOR MONITORING CELL MIGRATION AND IDENTIFYING CLINICALLY RELEVANT CYTOTOXIC T LYMPHOCYTE ACTIVITY

(75) Inventors: Dorothee Herlyn, Wynnewood, PA (US); Meenhard Herlyn, Wynnewood, PA (US); Rajasckharan Somasundaram, West Chester, PA (US)

(73) Assignee: The Wistar Institute, Philadelphia, PA (US)

( * ) Notice: Subject to any disclaimer, the term of this patent is extended or adjusted under 35 U.S.C. 154(b) by 665 days.

(21) Appl. No.: 10/488,949

(22) PCT Filed: Sep. 27, 2002

(86) PCT No.: PCT/US02/30767
§ 371 (c)(1),
(2), (4) Date: Nov. 22, 2004

(87) PCT Pub. No.: WO03/027256
PCT Pub. Date: Apr. 3, 2003

(65) Prior Publication Data
US 2006/0073469 A1    Apr. 6, 2006

Related U.S. Application Data

(60) Provisional application No. 60/324,907, filed on Sep. 27, 2001.

(51) Int. Cl.
*C12Q 1/00*   (2006.01)
*A01N 1/02*   (2006.01)

(52) U.S. Cl. ........................... 435/4; 435/1.1

(58) Field of Classification Search ........................ None
See application file for complete search history.

(56) References Cited

U.S. PATENT DOCUMENTS

| | | | |
|---|---|---|---|
| 4,835,102 A | 5/1989 | Bell et al. | |
| 5,688,927 A | 11/1997 | Godiska et al. | |
| 2003/0022279 A1* | 1/2003 | Fraser et al. | 435/69.1 |

FOREIGN PATENT DOCUMENTS

WO    WO 90/04398    *    5/1990

OTHER PUBLICATIONS

Kawakami et al, PNAS, 1994, vol. 91, pp. 3515-3519.*
Kawakami et al, PNAS, 1994, vol. 91, pp. 6458-6462.*
Abstract of Valyi-Nagy et al (Laboratory Investigation, Aug. 1993, 69(2):152-159).*
Jakic-Razumovic et al (Transplantation, 1995, vol. 59, pp. 69-78).*
Somasundarum et al (Int J Cancer, 2000, vol. 85, pp. 253-259).*
Entschladen et al (Cancer Research Clinical Oncology, 2000, vol. 126, pp. 671-681).*
Lazar-Molnar et al (Cytokine, Jun. 2000, vol. 12, pp. 547-554).*
Ueno et al (clinical Cancer Research, Aug. 2000, vol. 6, pp. 3282-3289).*
Bloom and Fawcett ('The Skin', In: A Textbook of Histology, 1962, pp. 372-391).*
Niggemann et al., "Locomotory phenotypes of human tumor cell lines and T lymphocytes in a three-dimensional collagen lattice," Cancer Letters 118 (1997) 173-180.
Rocha et al., "Lymphocyte migration into collagen gels: role of lymph," *Scand. J. Immunol*: 19, 297-305, 1984.
Schor et al., "The interaction of melanoma cells with fibroblasts and endothelial cells in three-dimensional macromolecular matrices: a model for tumour cell invasion," *Int. J. Cancer*: 36, 93-102 (1985).
Schor et al., "The use of three-dimensional collagen gels for the study of tumour cell invasion in vitro: experimental parameters influencing cell migration into the gel matrix," *Int. J. Cancer*: 29, 57-62 (1982).
Ratner et al., "T cell locomotion in the tumor microenvironment," Journal of Immunology, vol. 135, No. 3, 2220-2227, 1985.
Friedl et al., "Cell migration strategies in 3-D extracellular matrix: differences in morphology, cell matrix interactions, and integrin function," Microscopy Research and Technique, 43, 369-378 (1998).
Schor et al., "Lymphocyte migration into three-dimensional collagen matrices; a quantitative study," The Journal of Cell Biology, vol. 96, Apr. 1983, 1089-1096.
Berking et al., "Human skin reconstruct models: a new application for studies of melanocyte and melanoma biology," Histol. Histopathol (2001) 16: 669-674.
Meier et al., "Human melanoma progression in skin reconstructs," *American Journal of Pathology*, vol. 156, No. 1, Jan. 2000, pp. 193-200.
Wei et al., "A 3-dimensional tumor growth inhibition assay for testing monoclonal antibody cytotoxicity," Cancer Immunol. Immunother (1985) 20: 137-144.
Wei et al., "Inhibition of tumor growth by peptide specific cytotoxic T lymphocytes in a three-dimensional collagen matrix," Journal of Immunological Methods, 200 (1997) 47-54.
Allen et al., Scanning Electron Microscopy, An ultrastructural review of collagen gels, a model system for cell-matrix, cell basement membrane and cell-cell interactions, abstract, 1984, Pt. 1, pp. 375-390, Database Cancerlit on STN (Columbus, OH, USA), Acc. No. 84250006.
Friedl et al., Developmental Immunology, "T cell migration in three-dimensional extracellular matrix: guidance by polarity and sensations", abstract, 2000, vol. 7, No. 2-4, pp. 249-266, Database Lifesci on STN, CSA (Columbus, OH, USA), Acc. No. 2001:60131.
Database Medline on STN, US National Library of Medicine, Acc. No. 2001269689, Arihiro et al., "Cytokines facilitate chemotactic motility of breast carcinoma cells", abstract, Breat Cancer, 2000, vol. 7, No. 3, pp. 221-230.

* cited by examiner

*Primary Examiner*—Karen A Canella
(74) *Attorney, Agent, or Firm*—Banner & Witcoff, Ltd.

(57) ABSTRACT

A three-dimensional reconstruct model containing solid layers of collagen and fibroblasts closely mimic the condition of patients in vivo, preserving in vivo phenotypic and functional characteristics of the cells. Reconstructs can be used to detect cellular migration, including active migration of cytotoxic T lymphocytes towards tumor cells, which can be measured by detecting tumor cell lysis. Reconstructs also can be used to identify factors that influence migration of cells, including chemokines that influence migration of cytotoxic T lymphocytes, as well as to identify tumor antigens.

49 Claims, No Drawings

METHODS AND COMPOSITIONS FOR MONITORING CELL MIGRATION AND IDENTIFYING CLINICALLY RELEVANT CYTOTOXIC T LYMPHOCYTE ACTIVITY

This application is a National Stage application of co-pending PCT application PCT/US02/30767 filed Sept. 27, 2002, which was published in English under PCT Article 21(2) on Apr. 3, 2003, which claims the benefit of U.S. provisional application Serial No. 60/324,907 filed Sept. 27, 2001. These applications are incorporated herein by reference in their entireties.

This invention was made with government funds from grants 1 P50 CA 93372-01. The government has certain rights in the invention.

FIELD OF THE INVENTION

The invention relates to methods and compositions for monitoring cell migration and identifying clinically relevant cytotoxic T lymphocyte (CTL) activity.

BACKGROUND OF THE INVENTION

A critical issue in cancer immunotherapy is raised by the finding that tumors grow in patients even when infiltrated with lymphocytes. For example, a brisk pattern of T cell infiltration into vertical growth phase melanoma is a powerful predictor of cure after surgery (Clark et al., 1989). Nevertheless, tumors frequently progress (Lee et al., 1999b). Furthermore, results from melanoma antigen-specific vaccinations suggest vaccine effectiveness in eliciting T cell responses demonstrable in circulation and at the tumor site in the absence of clinical responses (Lee et al., 1999a; Finke et al., 1999; Nielson & Maricola, 2000). An important related question is why lymphocytes that lyse tumor targets in vitro often do not demonstrate therapeutic effects after adoptive transfer to patients in vivo (Maaser et al., 1999).

Multiple factors have been suggested to underlie the absence of CTL functions in vivo, such as (1) production of TGF-$\beta$ by tumor cells leading to impairment of CTL effector function, (2) downregulation of HLA class I on tumor cells in vivo leading to absence of tumor lysis by CTL, (3) absence of co-stimulatory molecules on tumor cells leading to impairment of CTL induction by direct tumor stimulation, (4) expression of Fas ligand by tumor cells leading to inactivation of Fas receptor-positive CTL, (5) emergence of tumor cell variants with epitope/antigen loss after tumor lysis by CTL in vivo, and (6) downregulation of $\zeta$ chain in CTL leading to loss of T cell function. All of these factors have been identified in vitro, but it is unclear which of them play a role in vivo. Elucidation of these questions would greatly impact T-cell based adoptive and active cancer immunotherapies.

These questions cannot be addressed directly in patients. Studies on T cell functions have been performed in tumors in situ using analyses of RNA expression (Finke et al., 1999). However, these studies have used biopsy material containing a mixture of cells and have used an RNA amplification method. Thus, the cell type which is the source of RNA (stroma cells, fibroblasts, tumor cells, immune effector cells) cannot be identified. Moreover, RNA amplification is non-linear and may be biased.

Thus far, relevant in vitro models are lacking. Traditionally, CTL are raised in two-dimensional mixed lymphocyte tumor cell culture (MLTC) that include either long-term cultured tumor cells to stimulate PBMC for CTL induction or disaggregated tumor tissue with tumor infiltrating lymphocytes (TIL), with both cultures grown directly on plastic surfaces. However, a study in melanoma patients has shown that characterization of CTL responses using tumor cell lines does not reflect the in vivo exerted anti-tumoral activity (Friedl et al., 1998). For example, melanoma-reactive human CTL derived from skin biopsies of delayed type hypersensitivity reactions, when stimulated with autologous long-term cultured tumor cells in vitro, demonstrated increased skewing of the V$\beta$ T cell receptor (TCR) repertoire with increasing time in culture (Rao et al., 2000). This suggests the selection of a CTL population in culture that does not reflect the composition of T lymphocytes in vivo. In agreement with that study, TCR expressed by CTL raised in MLTC are not expressed in situ (Crowston et al., 1997). Changes in TCR repertoire of CTL following in vitro culture indicate changes in antigen recognition. Thus, CTL in situ may recognize different antigens than CTL derived from long-term cultures.

In addition to the alterations of T cells in MLTC upon culture, the use of long term cultured tumor cells in MLTC is disadvantageous. For example, colorectal carcinoma (CRC) cells often lose HLA class I expression in culture, whereas the same tumors express these molecules in situ (Schroder, 1995). Similarly, the tumor suppressor gene p16 is expressed in ~70% of primary CRC, but in only ~10% of CRC cell lines (Luger & Schwarz, 1990). Furthermore, irradiated tumor cells often used in MLTC may not produce all of the factors that non-irradiated tumor cells produce; these factors may affect the induction or effector phase of CTL.

Chemokines play a major role in inducing migration of lymphocytes, neutrophils, monocytes, macrophages and dendritic cells to the tumor site. Chemokines may be incorporated into vaccines to increase vaccine efficacy at the site of the antigen-presenting cell or attached to an anti-tumor antibody to attract the effector cells to the tumor site. Alternatively, tumors may be transduced with chemokines to attract effector cells or CTL may be transduced with chemokine receptors (Biragyn & Kwak, 2000).

Thus, there is a need in the art for model systems that can be used to identify clinically relevant behaviors of CTL, including tumor cell lysis and active migration, as well as systems that can be used to identify chemokines that influence active migration of CTL towards tumor cells.

BRIEF SUMMARY OF THE INVENTION

One embodiment of the invention provides a composition of matter for detecting active migration of cells. The composition comprises (a) a first solid layer comprising collagen and fibroblasts, (b) a cellular layer in contact with the first solid layer and comprising a first cell type, (c) a second solid layer covering the cellular layer and comprising collagen and fibroblasts, and (d) a third solid layer in contact with the second solid layer and comprising collagen, fibroblasts, and a second cell type. The second cell type is a migratory cell. In a preferred embodiment, the first cell type is a tumor cell and the second cell type is a cytotoxic T lymphocyte.

Another embodiment of the invention provides a method of preparing a composition of matter. Collagen and fibroblasts are deposited in a vessel to form a first solid layer comprising collagen and fibroblasts. Cells of a first cell type are deposited on the first solid layer to form a cellular layer in contact with the first solid layer. Collagen and fibroblasts are deposited on the cellular layer to form a second solid layer comprising collagen and fibroblasts. The second solid layer covers the cellular layer. Collagen, fibroblasts, and cells of a second cell type are deposited on the second solid layer to form a third solid layer in contact with the second solid layer. The third solid layer comprises collagen, fibroblasts, and cells of the second cell type.

Even another embodiment of the invention provides a method of detecting active migration of migratory cells. First positions of migratory cells in the third solid layer of a composition are detected at a first time. Second positions of the migratory cells are detected at a second time. The compositions comprises (a) a first solid layer comprising collagen and fibroblasts, (b) a cellular layer in contact with the first solid layer and comprising a first cell type, (c) a second solid layer covering the cellular layer and comprising collagen and fibroblasts, and (d) a third solid layer in contact with the second solid layer and comprising collagen, fibroblasts, and the migratory cells. A difference in the first and second positions indicates active migration of the migratory cells. In a preferred embodiment, the first cell type is a tumor cell and the second cell type is a cytotoxic T lymphocyte.

Another embodiment of the invention provides a method of detecting active migration of cytotoxic T lymphocytes. A composition comprising (a) a first solid layer comprising collagen and fibroblasts, (b) a cellular layer in contact with the first solid layer and comprising tumor cells, (c) a second solid layer covering the cellular layer and comprising collagen and fibroblasts, and (d) a third solid layer in contact with the second solid layer and comprising collagen, fibroblasts is inspected to determine whether cytotoxic T lymphocytes are present in the second solid layer.

Yet another embodiment of the invention provides a method of detecting active migration of cytotoxic T lymphocytes towards tumor cells. Tumor cell lysis is detected in a first composition and a second composition. The first composition comprises (1) a first solid layer comprising collagen and fibroblasts, (2) a cellular layer in contact with the first solid layer and comprising tumor cells, (3) a second solid layer covering the cellular layer and comprising collagen and fibroblasts, and (4) a third solid layer in contact with the second solid layer and comprising collagen, fibroblasts, and cytotoxic T lymphocytes. The second composition comprises (1) a first solid layer comprising collagen and fibroblasts, (2) a cellular layer in contact with the first solid layer and comprising tumor cells, (3) a second solid layer covering the cellular layer and comprising collagen and fibroblasts, and (4) a third solid layer in contact with the second solid layer and comprising collagen, fibroblasts, and control lymphocytes that are not cytotoxic T lymphocytes. Increased tumor cell lysis in the first composition compared with the second composition indicates active migration of the cytotoxic T lymphocytes towards the tumor cells in the first composition.

A further embodiment of the invention provides a method of detecting cytotoxicity of cytotoxic T lymphocytes. A first percentage of killed tumor cells in a first composition is compared with a second percentage of killed tumor cells in a second composition. The first composition comprises (a) a first solid layer comprising collagen and fibroblasts, (b) a cellular layer in contact with the first solid layer and comprising tumor cells, (c) a second solid layer covering the cellular layer and comprising collagen and fibroblasts, and (d) a third solid layer in contact with the second solid layer and comprising collagen, fibroblasts, and cytotoxic T lymphocytes. The second composition comprises (a) a first solid layer comprising collagen and fibroblasts, (b) a cellular layer in contact with the first solid layer and comprising tumor cells, (c) a second solid layer covering the cellular layer and comprising collagen and fibroblasts, and (d) a third solid layer in contact with the second solid layer and comprising collagen, fibroblasts, and phytohemagglutinin-treated blast cells. An increase between the first and the second percentages indicates cytotoxic T lymphocyte-induced killing of tumor cells in the first composition.

Another embodiment of the invention provides a method of identifying a tumor antigen that binds to a T cell receptor of a cytotoxic T lymphocyte that induces killing of tumor cells. A clone of cytotoxic T lymphocytes that induces killing of tumor cells is identified by comparing a first percentage of killed tumor cells in a first composition with a second percentage of killed tumor cells in a second composition. The first composition comprises (a) a first solid layer comprising collagen and fibroblasts, (b) a cellular layer in contact with the first solid layer and comprising tumor cells, (c) a second solid layer covering the cellular layer and comprising collagen and fibroblasts, and (d) a third solid layer in contact with the second solid layer and comprising collagen, fibroblasts, and cytotoxic T lymphocytes. The second composition comprises (a) a first solid layer comprising collagen and fibroblasts, (b) a cellular layer in contact with the first solid layer and comprising tumor cells, (c) a second solid layer covering the cellular layer and comprising collagen and fibroblasts, and (d) a third solid layer in contact with the second solid layer and comprising collagen, fibroblasts, and phytohemagglutinin-treated blast cells. An increase between the first and the second percentages indicates cytotoxic T lymphocyte-induced killing of tumor cells in the first composition. Host cells that express an HLA restriction element autologous for the cytotoxic T lymphocytes and comprising cDNA of the tumor cells are tested to identify a host cell that induces cytokine release in cytotoxic T lymphocytes of the clone. Tumor cell cDNA is isolated from the host cell. The tumor cell cDNA encodes a tumor antigen. The invention also provides tumor antigens identified using such methods.

Even another embodiment of the invention provides a method of identifying a chemokine that influences active migration of migratory cells. A chemokine receptor expressed by a first population of migratory cells is identified. The first population is contacted with a molecule that specifically binds to the chemokine receptor. Active migration of the first population with active migration of a second population of migratory cells that has not been contacted with the first molecule. A difference in active migration between the first and second populations identifies the chemokine as influencing active migration of the migratory cells. Active migration of the first and second populations is detected by a method comprising the steps of: (1) detecting at a first time first positions of migratory cells in a third solid layer of a composition comprising (i) a first solid layer comprising collagen and fibroblasts, (ii) a tumor cell layer in contact with the first solid layer, (iii) a second solid layer covering the tumor cell layer and comprising collagen and fibroblasts; and (iv) the third solid layer in contact with the second solid layer and comprising collagen, fibroblasts, and cytotoxic T lymphocytes; and (2) detecting at a second time second positions of the migratory cells, wherein a difference in the first and second positions indicates active migration of the migratory cells.

Still another embodiment of the invention provides a method of identifying a chemokine or a cytokine that influences active migration of migratory cells. Active migration of a first population of migratory cells is compared with active migration of a second population of migratory cells. A difference in active migration between the first and second populations identifies the chemokine or the cytokine as influencing active migration of the migratory cells. Active migration of the first population is detected by a method comprising the steps of: (a) detecting at a first time first positions of the first population in a third solid layer of a first composition, wherein the first composition comprises (1) a first solid layer comprising collagen and fibroblasts, (2) a target cell layer in contact with the first solid layer, (3) a second solid layer covering the target cell layer and comprising collagen and fibroblasts; and (4) the third solid layer in contact with the second solid layer and comprising collagen, fibroblasts, and the first population, wherein the first composition further comprises a molecule that specifically binds to a chemokine or a cytokine; and (b) detecting at a second time second positions of the first population, wherein a difference in the first and second positions indicates active migration of the first population. Active migration of the second population is detected by a method comprising the steps of: (a) detecting at a first time first positions of the second population in a third solid layer of a second composition, wherein the second composition comprises (1) a first solid layer comprising collagen and fibroblasts, (2) a target cell layer in contact with the first solid layer, (3) a second solid layer covering the target cell layer and comprising collagen and fibroblasts; and (4) the third solid layer in contact with the second solid layer and comprising collagen, fibroblasts, and the second population; and (b) detecting at a second time second positions of the second population, wherein a difference in the first and second positions indicates active migration of the second population.

Yet another embodiment of the invention provides a method of identifying a chemokine that influences active migration of cytotoxic T lymphocytes towards tumor cells. Tumor cell lysis is detected in a first composition and a second composition. The first composition comprises (1) a first solid layer comprising collagen and fibroblasts, (2) a cellular layer in contact with the first solid layer and comprising tumor cells, (3) a second solid layer covering the cellular layer and comprising collagen and fibroblasts, and (4) a third solid layer in contact with the second solid layer and comprising collagen, fibroblasts, and a first population of cytotoxic T lymphocytes comprising a blocking molecule that prevents binding of the chemokine receptor to its cognate chemokine. The second composition comprises (1) a first solid layer comprising collagen and fibroblasts, (2) a cellular layer in contact with the first solid layer and comprising tumor cells, (3) a second solid layer covering the cellular layer and comprising collagen and fibroblasts, and (4) a third solid layer in contact with the second solid layer and comprising collagen, fibroblasts, and a second population of cytotoxic T lymphocytes, wherein the chemokine receptor of the second population is available to bind to its cognate ligand. The chemokine is identified as affecting migration of cytotoxic T lymphocytes if tumor cell lysis is greater in the second composition than the first composition.

Even another embodiment of the invention provides a method of identifying a cytokine that influences active migration of cytotoxic T lymphocytes towards tumor cells. Tumor cell lysis is detected in a first composition and a second composition. The first composition comprises (1) a first solid layer comprising collagen and fibroblasts, (2) a cellular layer in contact with the first solid layer and comprising tumor cells, (3) a second solid layer covering the cellular layer and comprising collagen and fibroblasts, and (4) a third solid layer in contact with the second solid layer and comprising collagen, fibroblasts, and a first population of cytotoxic T lymphocytes, wherein the first composition further comprises a blocking molecule that prevents binding of a cytokine to its cognate receptor. The second composition comprises (1) a first solid layer comprising collagen and fibroblasts, (2) a cellular layer in contact with the first solid layer and comprising tumor cells, (3) a second solid layer covering the cellular layer and comprising collagen and fibroblasts, and (4) a third solid layer in contact with the second solid layer and comprising collagen, fibroblasts, and a second population of cytotoxic T lymphocytes, wherein cytokines in the second composition are available to bind to their cognate receptors. The cytokine is identified as affecting migration of cytotoxic T lymphocytes if tumor cell lysis is greater in the second composition than the first composition.

The invention thus provides methods and compositions for detecting active migration of cells, particularly CTL, and identifying clinically relevant behaviors of CTL.

DETAILED DESCRIPTION OF THE INVENTION

We have developed novel human organotypic culture systems, termed "reconstructs," that closely mimic the conditions in patients in vivo, so that the in vivo phenotypic and functional characteristics of the cells are preserved as much as possible. In the three-dimensional reconstruct, tissues such as human tumors, particularly melanoma and colorectal carcinoma (CRC), are reconstituted in vitro using a mixture of collagen and fibroblasts (lattices or matrices).

Activated fibroblasts in reconstructs play an important role in the activation of T cells. The fibroblasts produce T cell survival factors (Murakami & Okada, 1997) and fibronectin, the latter stimulating predominantly resting lymphocytes (Somasundarum et al., 2000). In addition, fibroblasts produce various cytokines, growth factors and chemokines (Jacobs et al., 1998; Jakic-Razumovic et al., 1995; Gunzer et al., 2000). CRC-derived factors may exert inhibitory (e.g., TGF-β or IL-10) or stimulatory (e.g., IL-1 and GM-CSF) effects on T cell induction. Some of the factors produced by fibroblasts and CRC cells may affect the induction, as well as the effector phase of T lymphocytes in the reconstruct. Very little is known about the factors that affect the effector phases of CTL because the relevant assays (e.g., $^{51}$Cr-release assay) do not allow the determination of these effects.

Lymphocytes bind to fibroblasts via lymphocyte function-associated Ag-1 (LFA-1), intercellular adhesion molecule-1 (ICAM-1) and CD44. The adhesive interaction stimulates fibroblasts to secrete inflammatory cytokines such as IL-1 and IL-6 (Biragyn & Kwak, 2000). The main biological role of IL-1 is the stimulation of Th cells to express IL-2 receptors and secrete IL-2 (Herlyn et al., 2000). In addition, IL-1 can promote adhesion of T cells by upregulation of adhesion molecules such as ICAM-1, VCAM (vascular cell adhesion molecule)-1 and ELAM (endothelial leukocyte adhesion molecule). In the presence of IL-2 and IL-6, IL-1 induces the differentiation of T cells into cytotoxic T cells (Herlyn et al., 2000).

By investigating CTL functions in reconstructs, new combination therapies (e.g., with cytokines and/or chemokines) that may augment the cytolytic function of CTL in patients can be developed. For example, examination of CTL induction in the reconstruct can be used to identify novel factors, not previously identified in traditional mixed lymphocyte tumor culture (MLTC), which may be useful for enhancing the vaccine effect of CTL-derived antigens. Furthermore, CTL that are raised against fresh tumor tissues may recognize different, clinically more relevant antigens than the CTL raised in traditional MLTC, in which tumor cells and lymphocytes are cocultured directly on plastic surfaces. Identification of the most effective CTL directed against fresh tissues in a reconstruct model may lead to more effective adoptive CTL and vaccination immunotherapies as compared to conventional strategies based on MLTC-derived CTL.

Reconstruct models have several advantages over conventional in vitro assays (4 or 18 hr $^{51}$Cr-release assay) and in vivo/in situ assays (11) (see Table 1). The cytolytic functions of T cells are usually tested in vitro in $^{51}$Cr release assay. However this assay does not mimic the in vivo situation. First, it is of short duration and therefore may not allow detection of antigenic modulation of tumor cells, including tumor antigens and HLA, as well as studies on the effect of cytokines produced by tumor cells on CTL effector function. Second, it includes single tumor cell suspensions and not tumor tissues, thus not allowing detection of eventual negative effects of the growing tumor on T cell function. Third, the $^{51}$Cr-release assay uses artificially high E:T cell ratios. Fourth, the assay does not take into account T cell migration into tumor tissues. Furthermore, studies of T cell kinetics, e.g. the kinetics of direct tumor cell lysis by CTL over time can only be studied in the reconstruct model. This model is also advantageous for studies on the mechanism of tumor cell lysis by CTL with the ultimate goal of enhancing CTL function in adoptive immunotherapies of cancer patients.

TABLE 1

Advantages of reconstruct models for characterizing CTL activity

| | Assay systems | | |
|---|---|---|---|
| Parameter | $^{51}$Cr release (CTL) assay | Reconstruct | In vivo/in situ assays |
| Tumor or T cell/stroma interaction | no | yes | yes |
| T cell kinetic | no | yes | no |
| Time period of T cell/tumor cell interaction | 4-18 hr | 4 weeks | indefinitely |
| T cell migration | no | yes | no |
| Mechanism of tumor killing by T cells | biased (in vivo factors neglected) | yes | limited |
| Manipulation of T and/or tumor cells | biased (in vivo factors neglected) | yes | limited |
| Required CTL to tumor cell ratio | high (>20) | low (<1) | unknown |
| Determination of effect of cytokines and chemokines on T cell function | no | yes | no |

Reconstructs and their Preparation

Compositions of the invention ("reconstructs") comprise four layers. One layer (the "first solid layer") comprises collagen and fibroblasts. A "cellular layer" is in contact with the first solid layer and comprises a first cell type, also termed herein a "target cell." A "second solid layer" covers the cellular layer and comprises collagen and fibroblasts. Finally, a "third solid layer" is in contact with the second solid layer. The third solid layer comprises collagen, fibroblasts, and a second cell type.

Typically, neutralized type I collagen is used in layers of a reconstruct. Fibroblasts can be obtained from a variety of sources, including primary tissues (e.g. human neonatal foreskin) and fibroblast cell lines derived from neonatal human foreskin (e.g., FF2443).

In preferred embodiments, the first cell type is a tumor cell, such as a cell of a colon tumor, biliary tumor, brain tumor (e.g., glioblastoma, medulloblastoma), breast tumor, cervical tumor, choriocarcinoma, endometrial tumor, esophageal tumor, gastric tumor, hematological cancer (e.g., acute lymphocytic and myelogenous leukemia, multiple myeloma, AIDS associated leukemias, adult T-cell leukemia, lymphoma), intraepithelial tumor, liver tumor, lung tumor, neuroblastoma, ovarian tumor, pancreatic tumor, prostate tumor, rectal tumor, sarcoma (including leiomyosarcoma, rhabdomyosarcoma, liposarcoma, fibrosarcoma and osteosarcoma), skin tumor (including melanoma), testicular tumor, renal tumor, bladder carcinoma, or choriocarcinoma. Either primary tumor cells or tumor cell lines can be used. For example, suitable colon tumor cell lines are described in Example 5.

The second cell type typically is a migratory cell, such as a leukocyte (e.g., a neutrophil, macrophage, dendritic cell, or monocyte) or lymphocyte (e.g., a natural killer cell or lymphocyte, particularly a cytotoxic T lymphocyte (CTL).

Reconstructs can be prepared as follows. Briefly, collagen and fibroblasts are deposited in a vessel to form the first solid layer. Wells of a 24-well plastic tissue culture plate provide a convenient vessel, although other plastic or glass vessels can be used. Target cells are deposited on the first solid layer to form the cellular layer. The second solid layer, which covers the cellular layer, is formed by depositing collagen and fibroblasts on the cellular layer. Finally, collagen, fibroblasts, and a second cell type are deposited on the second solid layer to form the third solid layer. Methods of preparing reconstructs are described in detail in the specific examples, below.

Methods of Detective Active Migration

Compositions of the invention can be used to detect active migration of cells, such as leukocytes (e.g., neutrophils, macrophages, or monocytes) or lymphocytes (e.g., natural killer cells or lymphocytes, particularly CTLs). Positions of migratory cells are detected at a first time in the third solid layer of a composition of the invention. Positions of the migratory cells are detected at a second time. A difference in the first and second positions indicates active migration of the migratory cells. For example, in one embodiment, human dermis is recapitulated in vitro using mixture of collagen and fibroblasts (lattices or matrices). Melanoma cells can be included in the reconstruct. Melanoma cell migration through collagen matrix, which is dependent on the interaction of α2β1 integrin (expressed by melanoma cells with collagen (Maaser et al., 1999), can be detected.

One or more compositions can be used to detect a difference in the positions of migratory cells. For example, compositions can be fixed and sectioned, and the cells can be stained by conventional histological techniques, as described in the specific examples, below.

Use of Reconstruct Models to Identify Factors that Modulate CTL Activity and Migration Reconstructs of the invention can be used to identify factors that activate or inhibit CTL activity against tumor cells in vivo or which modulate CTL migration. The identification of these factors can greatly impact adoptive immunotherapy with CTL and active immunotherapy with CTL-defined antigens. For example, factors that enhance CTL induction and/or effector function in the reconstruct can be added to adoptive and active immunotherapies. Factors that impair CTL induction and/or effector function can be functionally inactivated by CTL manipulation ex vivo (adoptive CTL transfer) and/or tumor modulation in vivo (gene therapy).

The effector lytic mechanisms of CTL are usually tested in 6 hr or overnight $^{51}$Cr-release assays. Chromium-release assays are unsatisfactory for identifying relevant factors, however, because the tumor cells are in contact with the CTL for too short a time and fibroblast are absent. In contrast, the importance of fibroblast- and tumor-derived factors for CTL activity can easily be evaluated in reconstructs. In fact, additional CTL and/or tumor markers should be expressed in a reconstruct because fibroblasts produce various cytokines and growth factors and because collagen stimulates T cells (18). This is supported by the fact that the minimally required E:T ratio to induce tumor lysis by CTL is much lower in a reconstruct than in an MLTC.

Factors that potentially play a role in the activity of CTL in a reconstruct model include, but are not limited to, CD markers (e.g., CD3, CD4, CD8, CD25/IL2-Rα, CD45, CD45RO, CD28), adhesion molecules (e.g., E-cadherin, CD44, CD54/ICAM 1/My13, CD11a/LFA 1, CD106/VACAM/51-10C9, CD29/β1 integrin for VCAM, β3 integrin), HLA (e.g., class I, class II, β2 microglobulin/BM63), co-stimulatory molecules (e.g., CD80/B7-1, CD86/B7-2) tumor antigens (e.g., MAGE-1, tyrosinase, MART/MELAN A, p91A, MUM-1, p21$^{ras}$ with a point mutation at position 12, p210 product of bcr-abl rearrangements, HER-2/neu, p53, RB, BAGE, GAGE, SV40 T antigen, human papillomavirus E6 and E7 gene products, Epstein-Barr virus EBNA-1 gene product), apoptosis/necrosis molecules (e.g., FAS, FAS-L, granzyme B, perforin, TNF-α), cytokines (e.g., GM-CSF, TFN, IFNγ, IL-1, IL-2, IL-4, IL-6, IL-8, IL-10, TNF-α), chemokines and their receptors (e.g., IP-10, MIP-1α, CCR5/MCP-1α, RANTES receptor, RANTES, CCR1/MCP-1 receptor, CCR-2/MCP-1 receptor, CXCR1/IL-8 receptor; for a complete list, see Homey et al., 2002), and growth factors (e.g., TGFβ).

Reconstruct models described herein are particularly useful for identifying the role of individual cytokines and chemokines in CTL migration. For example, cytokines that are secreted by fibroblasts or tumor cells and that modulate CTL induction or effector function against tumor cells can be identified. Cytokines that directly potentiate CTL effector function are largely unknown. Other cytokines may directly induce target cell necrosis, such as TNF and IFNγ.

In one embodiment, reconstructs are formed with and without the inclusion of fibroblasts. If omission of fibroblasts in such reconstructs affects CTL effector function, techniques such as microarray analysis and IHC can be used to identify which cytokines are expressed by fibroblasts isolated from the reconstruct. Antibodies penetrate through the collagen/fibroblast matrix of a reconstruct. Thus, identified cytokines can be inactivated using neutralizing antibodies, and the effect of such inactivation on the migration of CTL toward tumor cells can be determined in a reconstruct model. The identified cytokines can be used in conjunction with adoptive CTL immunotherapy or as adjuvants with vaccines of CTL-defined antigens.

Reconstructs also are unique in their ability to permit investigation of the role of chemokines and their receptors in the migration of CTL towards tumor cells. Chemokines control leukocyte and activated T cell migration to sites of inflammation and immune reaction. Fibroblasts present in a reconstruct may be stimulated by IL-1 (produced by tumor and/or T cells) to produce chemokines (e.g., MIP-1α, MCP-1, RANTES) that may stimulate CTL migration. However, because fibroblasts typically are evenly dispersed throughout all layers of a reconstruct, they will not necessarily provide a chemokine gradient. In contrast, tumor-derived chemokines can provide a gradient, which will attract the T cells and cause T cell migration from a distant layer to the tumor layer, resulting in tumor apoptosis.

Thus, reconstructs can be used to identify the chemokines and/or chemokine receptors that are involved in the migration of CTL. Chemokine receptors expressed by CTL can be identified, for example, using antibodies. Antibodies can be obtained from commercial sources (e.g., R&D Systems, Inc., Minneapolis, Minn.) or can be raised using standard technologies. Alternatively, RT-PCR using known primers can be used.

Recognizing that one receptor can bind several chemokines, an ELISA assay can be used to determine whether tumor cells secrete a corresponding chemokine into serum-free medium.

Blocking molecules, such as chemokine antagonists or antibodies, can be used to block the identified receptor to test the effect of blocking binding between an identified chemokine and its receptor. In one embodiment, CTL are incubated with an antibody (e.g at 0.5 μg/ml final concentration) before they are placed in a reconstruct. Inhibition of CTL migration relative to isotype-matched control antibody at the same concentration can be determined by measuring inhibition of tumor cell apoptosis. If tumor cell apoptosis is greater in the control reconstruct, the chemokine is identified as involved in active CTL migration toward the tumor cells.

To confirm the role of the chemokine in CTL migration, the chemokine itself can be blocked using chemokine-specific antibodies or other molecules that bind to the chemokine and prevent its binding to its receptor. To further confirm the role of the identified chemokine in CTL migration and induction of tumor cell apoptosis, the chemokine can be added to a layer of tumor cells in a reconstruct (e.g., at 1-10 μg/ml), which should increase both CTL migration toward the tumor cells and tumor cell apoptosis. Finally, if the identified chemokine enhances CTL migration, transfection of the identified chemokine into tumor cells to overexpress the chemokine will lead to enhanced tumor cell apoptosis induced by CTL. Transfection can be achieved, for example, using a vector, such as an adenovirus vector, that expresses the chemokine.

Relevant cytokines or chemokines identified in a reconstruct model can, for example, be fused to a tumor-specific antibody to attract adoptively transferred CTL or can be incorporated into vaccines to activate T cells (Biragyn & Kwak, 2000). Alternatively, a tumor can be transduced with one or more chemokines or cytokines in vivo or CTL may be transduced with chemokine or cytokine receptors.

Methods of Detecting Cytotoxicity of CTLs

Cytotoxicity of CTLs against target cells (e.g., tumor cells) in the cellular layer of a reconstruct can be detected by any means known in the art, including biochemical and morphological methods. See the specific examples, below. For example, apoptotic tumor cells can be detected in a TUNEL assay or by microscopic examination.

In one embodiment, pairs of reconstructs comprise either CTL or phytohemagglutinin (PHA)-treated blast cells, preferably obtained from the same individual. The percentage of killed tumor cells are detected and compared between the two reconstructs. An increase between the percentage of killed cells in the reconstruct comprising CTL and the percentage of killed cells in the reconstruct comprising the control cells indicates cytotoxicity of the CTLs against the tumor cells. Alternatively, the percentages of viable cells in the two cellular layers can be compared. In another embodiment, the percentage of killed tumor cells (or remaining viable cells) in a series of reconstructs is detected over various times.

Methods of Identifying Tumor Antigens

Effective CTLs identified using reconstructs of the invention can be used to identify tumor antigens. Tumor antigens are antigens that are expressed either only on tumor cells but not on normal cells or are expressed are a greater level on tumor cells compared with normal cells. Preferably, tumor antigens stimulate T cell responses. Examples of such tumor antigens include products of random point mutations in cellular genes (e.g. p91A, MUM-1), oncogene products (e.g., p21$^{ras}$ with a point mutation at position 12, p210 product of bcr-abl rearrangements, HER-2/neu), mutated tumor-suppressor gene products (e.g., p53, RB), products of silent genes not normally expressed in most tissues (e.g., MAGE 1, -3, BAGE, GAGE), viral gene products in virus-associated malignancies (e.g., SV40 T antigen, human papillomavirus E6 and E7 gene products, Epstein-Barr virus EBNA-1 gene product), and products of tissue-specific genes expressed in the tissue from which a tumor is derived (e.g., tyrosinase, p100, MART-1). Tumor antigens that stimulate CTL responses can be used in the preparation of therapeutic compositions.

CTL antigens usually are recognized by HLA class I-restricted $CD8^+$ or $CD4^+$ CTL (Somasundarum et al., 2000; Jacob et al., 1997; townsend et al., 1986; Yasukawa et al., 1989; hayashi et al., 1992; Go et al., 1993) and less frequently by HLA non-restricted $CD8^+$ CTL (Band et al., 1989). In one embodiment, cDNA encoding the autologous HLA restriction element and a library of autologous tumor cell cDNA library is co-transfected into host cells (e.g., COS cells). Pools of cDNA are tested for reactivity with CTLs, for example in a cytokine release assay. Reactive cDNA clones are isolated, and the encoded antigen is characterized. Details are provided in the specific examples, below.

A peptide isolation method also can be used to identify tumor antigens, as is well known in the art. See Weber, 2002.

All patents, patent applications, and references cited in this disclosure are incorporated by reference in their entireties.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

EXAMPLE 1

Identification of CTL Against Human Melanoma Cells

Melanoma patient 793 had a primary vertical growth phase (VGP) tumor which was excised in 1983 and has been in remission since. PMBC obtained from patient 793 in 1989 were stimulated with autologous melanoma cells 793 (from day 0 on) and IL-2 (from day 7 on). Three $CD4^+$ clones with cytolytic activity against autologous tumor cells were isolated, of which one (clone A) was studied in detail. CTL793 clone A lysed the autologous melanoma cells WM793, but not the metastatic variant cells 1205Lu derived from serial passages of WM793 cells both in vitro and in vivo in nude mice (Juhasz et al., 1993), although the variant cells express the same HLA as the parental cells.

There was no significant lysis of autologous Epstein Barr virus (EBV)-B cells or NK- or LAK-sensitive target cells. These findings were further confirmed in cytokine (IFN-γ) release assays. Of the various allogeneic melanoma cells used as targets in CTL assays, only three that share HLA B57[17] with the autologous WM793 cells were consistently and significantly lysed and lysis was blocked by anti-B57[17] MAb (as well as by anti-CD3, -CD4 and -class I MAbs).

To confirm HLA B57[17] dependency of target cell lysis, HLA B57 was cloned from WM793 cells and transfected into allogeneic, HLA non-matched WM1158 melanoma cells. Transfected, but not non-transfected, WM1158 cells were significantly lysed by CTL 793 clone A.

Thus, the $CD4^+$ CTL 793 clone A described here clearly interacts with HLA class I molecules in the lysis of melanoma cells. Characterization of CTL clone 793A is shown in Table 2.

TABLE 2

Characteristics of melanoma cells and anti-melanoma CTL

| | Cell line/clone | | |
|---|---|---|---|
| Marker | WM793 | $CD4^+$ 793 CTL clone A | $CD8^+$ 793 CTL |
| HLA (% pos. cells) | | | |
| HLA class I | >95 | >95 | >95 |
| HLA class II | >90 | 74 | >95 |
| CD markers (% pos. cells) | | | |
| CD3 | – | >99 | >90 |
| CD4 | NA | >99 | <1 |
| CD8 | NA | <1 | >98 |
| Co-stimulatory molecules (% pos. cells) | | | |
| B7-1 | 7 | 6 | NT |
| B7-2 | 3 | 4 | NT |
| CD40 | 3 | 14 | NT |
| CD40-L | 6 | 24 | NT |
| Adhesion molecules (% pos. cells) | | | |
| β1 integrin | 100 | 60 | NT |
| CD44 | 92 | 97 | NT |
| CD54 (ICAM) | >95 | <20 | NT |
| Cytokines (RIA/ELISA/FACS) | | | |
| IFNγ | – | + | + |
| TNFα | – | + | + |
| GM-CSF | – | + | + |
| TGFβ | + | – | – |
| IL-1 | + | – | – |
| IL-2 | – | – | – |
| IL-4 | – | – | – |
| IL-8 | + | – | NT |
| IL-10 | – | – | NT |
| Apoptosis markers (% pos. cells) | | | |
| FAS | >95 | >95 | NT |
| FASL | 10 | <5 | NT |
| Chemokines | | | |
| MCP-1 | + | NT | NT |
| Rantes | NT | NT | NT |
| MIP-1α | – | NT | NT |
| Chemokine receptors | | | |
| CCR1 | NT | + | NT |
| CCR2 | NT | + | NT |
| CCR5 | NT | + | NT |

NT = not tested;
NA = not applicable.

EXAMPLE 2

Generation of $CD8^+$ CTL $CD8^+$ CTL were generated from the PBMC of primary melanoma patient 793 in an MLTC, and IL-2 was added to the cultures as early as day 3. The phenotype of this CTL population is predominantly (>80%) $CD8^+$. The $CD8^+$ CTL were reactive in $^{51}$Cr-release and/or cytokine release assays against allogeneic melanoma cells matched with autologous melanoma cells at HLA-A1, A29, or B57[17] loci. Thus, the uncloned CTL may recognize several antigens/epitopes in association with different HLA. There was no significant reactivity of the $CD8^+$ CTL with NK, LAK or autologous and nine different allogeneic EBV-B targets. The phenotypic and functional markers of the $CD8^+$ CTL 793 are summarized in Table 3.

TABLE 3

Lysis of various HLA-matched and -unmatched target cells and IFN-γ secretion by CD8+ 793 CTL

| Target cell | | | % Maximal cytotoxicity[b] | IFN-γ secretion (U/ml)[c] |
|---|---|---|---|---|
| Designation | Origin | HLA subtype[a] | | |
| WM793 | autologous primary melanoma | A1, A29, B57[17], B35, DRB1 11, DQB1 0301 | 40.1[d] | 10[d] |
| DM196 | allogeneic metastatic melanoma | A23(9), Aw34, B57[17], B44, DR1, DR3, DRw1, DRw52 | N.D.[e] | 2.2[d] |
| ME9874 | allogeneic metastatic melanoma | A2, A24, B57[17], B60, Cw3, Cw7, DR7, DQ2 | 8.3[d] | 5.9[d] |
| A375 | allogeneic metastatic melanoma | A1, A2, B57[17], —, C6, — | N.D. | 41.2[d] |
| 1205LU[f] | autologous metastatic variant | A1, A29, B57[17], B35, DRB1 11, DQB1 0301 | 6.6 | <0.01 |
| WM75 | allogeneic metastatic melanoma | A2, A29, B12w44, DR4, DR7 | 24.2[d] | 4.6[d] |
| WM98 | allogeneic metastatic melanoma | A1, A3, B8, DR3 | 8.1 | <0.01 |
| WM164 | allogeneic metastatic melanoma | A24, —, B7, —, C7, —, DR13, —, DQ1, DQ6, DRw52 | N.D. | <0.01 |
| WM1158 | allogeneic metastatic melanoma | A11, A24, B16, B60(40), C3, —, DR13, DR4, DQ3, DQ6, DRw52, DRw53 | 45[d] | <0.01 |
| 793 EBV-B | autologous B cells | A1, A29, B57[17], B35, DRB1 11, DQB1 0301 | 0 | 1.3 |
| 888EBV-B | allogeneic B cells | A1, A24, B52, B55, C1, C7, DR15, — | N.D. | <0.01 |
| 1363EBV-B | allogeneic B cells | A1, A2, B44, B51, C1, —, DR1, — | N.D. | <0.01 |
| 1088EBV-B | allogeneic B cells | A1, A2, B8, B44, C5, —, DR4, DR17 | N.D. | <0.01 |
| 1102EBV-B | allogeneic B cells | A2, A24, B55, B62, C3, —, DR4, DR15 | N.D. | <0.01 |
| 4226EBV-B | allogeneic B cells | A24, A32, B27, B38, C3, —, DR4, DR15 | N.D. | <0.01 |
| K562 | NK-sensitive erythroleukemia cells | N.D. | 0 | <0.01 |
| Daudi | lymphokine-activated killer cell-sensitive lymphoma cells | N.D. | 0 | <0.01 |

[a]Based on tumor cell typing, except for WM75, WM98, DM196, DM198, ME9874. HLA types of WM793 cells and those matching between WM793 and other cells are in bold.
[b]CTL culture supernatants obtained after 24 hr of stimulation with various stimulator cells and IFNγ were tested for cytokine production by RIA.
[c]Lysis of labeled tumor target cells was determined in $^{51}$Cr release assay.
[d]$p < 0.05$ when compared to corresponding cpm values of spontaneous release of $^{51}$Cr by target cells and/or spontaneous release of cytokine by CTL.
[e]ND, not determined.
[f]Metastatic variant cells 1205LU were derived from primary WM793 cells by serial passage of these cells both in vitro and in vivo in nude mice (Juhasz et al., 1993).

EXAMPLE 3

CD4+ CTL 3122 Derived from Lymphocytes Infiltrating a Melanoma Spleen Metastasis CD4+ CTL were generated from the lymphocytes infiltrating spleen metastases of a melanoma patient by repeated stimulation of the CTL with metastatic melanoma cell line WM3122 and IL-2. When tested for cytotoxicity in a $^{51}$Cr-release assay, the short-term CTL line (2-3 months in culture) significantly lysed the autologous melanoma cells and not allogeneic melanoma cells (WM793) or NK cell target (K562). The phenotype of this cell line was predominantly CD4+ (>75% of the cells).

EXAMPLE 4

T Cells Derived from Melanoma-Infiltrated Lymph Nodes

Tumor-infiltrated lymph nodes from patients 3406, 3407, 3408, and 3409 were used to generate CTL. Mechanically disaggregated cells were incubated for 7 days, followed by repeated IL-2 stimulations every 7 days. On day 28, T cells were restimulated with short-term cultured autologous melanoma cells and IL-2. These lymphocytes were both CD4+ and CD8+. TIL 3406 significantly lysed autologous melanoma cells in a $^{51}$Cr-release assay.

EXAMPLE 5

Establishment of Primary Colorectal Carcinoma Cell Lines

Colorectal carcinoma cell lines were established by mincing the tissue in Leibovitz/MCDB medium supplemented with 5% fetal bovine serum, 400 mM L-glutamine, 5.6% NaHCO$_3$, 5 mg/ml streptomycin, 10,000 U/ml penicillin, 250 µg/mg fungizone, and 5 mg/ml insulin, and plating the cells in the same medium in 24-well plates pre-coated with 1% gelatin, followed by incubation in a 5% CO$_2$ incubator. Medium of the cultures was changed weekly, and confluent cultures were subcultured with trypsin.

In most cases, the HLA phenotypes of patients, as determined in complement-dependent cytotoxicity or by PCR using allele-specific primers (HLA DR, DP, and DQ), were confirmed for autologous tumor cells by FACS or PCR analyses using allele-specific monoclonal antibody (MAb) or primers, respectively. Some HLA types were expressed on the CRC lines only after treatment of these cells with IFN-γ.

All cell lines expressed the CRC-associated antigen C017-1A/GA733 and all WC lines were tumorigenic in either nude or SCID mice.

TABLE 4

Primary CRC cell lines

| CRC line | Tissue of origin | Patients' HLA-types and HLA expression by tumor cells | | | | | |
|---|---|---|---|---|---|---|---|
| | | A | B | Cw | DR | DP | DQ |
| WC007 | rectum, primary | 1, $3^2$ | 35 | n.e.[1] | $DR^2$, $1^3$, $4^2$ | n.e. | n.e. |
| WC008 | rectum, primary | $1^2$, 3 | 57(17) | n.e. | $DR^2$, $7^3$ | n.e. | n.e. |
| WC010 | rectum, primary | $25^3$, $29^3$, $3^3$ | $18^3$, $58^3$(17) | $3^3$ | $7^3$, $9^3$ | n.e. | n.e. |
| WC011 | colon, primary | $19^3$ | 5 or 21 | $7^3$, $8^3$ | $2^3$, $11^3$(5) | n.t.[4] | n.e. |
| WC012 | colon, primary | 2 | 14, 35 | $7^3$, $8^3$ | $1^5$ (0101/0102/0104), $14^5$ (1401/1407) | n.e. | n.e. |
| WC013 | colon, primary | 1, 32(25) | $22^3$, 44(12) | $3^3$, $4^3$ | 3, 13(6) | n.e. | n.e. |
| WC016 | colon, primary | $2^3$, 3 | $5^3$, $41^3$ | $6^3$, $7^3$ | n.e. | n.e. | n.e. |

[1] n.e. = not expressed on tumor cells.
[2] Expression on tumor cells only upon IFN-γ treatment.
[3] HLA types are derived from lymphocytes and tumor expression has not yet been verified.
[4] n.t. = not tested.
[5] Expression verified by PCR only.

EXAMPLE 6

Cytotoxicity of CTLs in Tumor Reconstruct Models

CD4+ CTL that were generated from the PBMC of primary melanoma patient 793 in MLTC were tested for the ability to induce growth regression of autologous melanoma cells in a human dermis reconstruct model. Human dermis reconstructs were made by mixing normal human skin fibroblasts with type I collagen, and collagen was allowed to constrict in Dulbecco's modified Eagle's medium (DMEM) supplemented with 10% human AB serum. After 24 hr, WM793 cells ($1\times10^5$) were seeded on each contracted collagen matrix, and the gel was allowed to attach and grow in tumor/fibroblast (1:1) medium. After 24 hr, an equal number of CTL ($1\times10^5$) was mixed with normal fibroblasts and collagen gel and layered on top of the collagen-tumor gel. Thus, CTLs need to migrate through collagen layer to reach the melanoma cells.

Collagen cultures were maintained for 4 more days until cell harvesting and/or fixation. In control experiments, CTL were replaced by equal numbers of T cell blasts derived by stimulating 793 PBMC with 1% v/v PHA-M (Gibco) for 72 hr and further propagation in IL-2 containing medium. Reconstructs were stained on day 7 with hematoxylin and eosin.

Cultures containing autologous PHA blasts contained large numbers of healthy WM793 tumor cells. In contrast, the dermis reconstruct culture established with 793 CTL contained predominantly dead tumor cells. In many areas of the CTL reconstruct cultures, the melanoma cells had completely disappeared, whereas a continuous layer of live melanoma cells was seen in the control cultures. Notably, E:T ratio of 1 was highly effective in the reconstruct, while only marginally effective in MLTC (Somasundarum et al., 2000).

An apoptosis (TUNEL) assay demonstrated that experimental tumor cell cultures undergo significantly higher rates of apoptosis in the reconstruct as compared to control tumor cell cultures ($p<0.05$; Student's t-test). CD25 (IL-2 receptor) staining of the control cultures revealed little non-specific staining (probably of dying PHA blasts), whereas there was strong staining of CTL 793. There was no significant staining with isotype-matched control antibody.

RNA was isolated from CTL 793 grown for 5 days in the melanoma/dermis reconstruct. PCR analysis of cDNA using CD3 primers revealed that the RNA was derived from T cells.

EXAMPLE 7

Melanoma Dermis Reconstruct and Immunohistochemistry (IHC)

Normal human fibroblasts (FF2443) are isolated from the dermis of neonatal human foreskins, cultured in DMEM with glutamine (Gibco/BRL, Gaithersburg, Md.), 8 mM HEPES (Sigma, St. Louis, Mo.), and 10% fetal bovine serum (FBS) (Hyclone, Logan, Utah). WM793 cells are cultured in 4 parts MCDB153 (Sigma) and 1 part L15 medium (Gibco) supplemented with 2% FBS and 5 μg/ml insulin (Sigma). To determine the effect of IL-2 on CTL function in reconstruct, CTL are stimulated with autologous tumor cells for 4 days before incorporating them into the tumor (e.g., melanoma or colorectal carcinoma) reconstructs. Control T cell blasts are derived by stimulating PBMC with T cell mitogen (1% v/v PHA-M, Gibco) for 72 hr followed by cultivation in IL-2 containing medium.

Normal human skin fibroblasts (FF2443) are added to neutralized type I collagen (Organogenesis, Canton, Mass.); final concentration of 0.8-1 mg/ml) in minimal essential medium (MEM) (BioWhittaker, Walkersville, Mass.), 1.66 mM L-glutamine (Gibco), 10% human AB serum and 0.21% sodium bicarbonate (BioWhittaker). Three hundred-fifty μl of fibroblast-containing collagen ($1.4\times10^5$ cells per ml) are added per well of a 24-well tissue culture plate (Falcon, Becton Dickinson, Franklin Lakes, N.J.). The mixtures are allowed to constrict in DMEM with 10% human AB serum.

After 24 hr, a total of $1\times10^5$ WM793 cells (Hsu et al., 1999) are seeded on each contracted collagen matrix and allowed to attach for 2 hr. Following incubation, the culture medium is exchanged by one part DMEM supplemented with 10% human AB serum and mixed 1:1 with melanoma cell culture medium supplemented with 2% human AB serum. After 24 hr, 250 µl of type I collagen mixed with FF2443 ($1.5 \times 10^5$ cells per ml) and a total of $1 \times 10^5$ lymphocytes are added to the collagen/fibroblast/melanoma cultures and allowed to constrict.

Cultures are maintained submerged in the medium supplemented with 2% human AB serum for 4 more days until cell harvesting and/or fixation. Reconstructs are fixed in 10% neutral-buffered formalin (Fisher Scientific, Pittsburgh, Pa.) for 4 hr at room temperature, stored in 70% ethanol at 4° C. and embedded in paraffin. For frozen sections, tissues are dehydrated in increasing concentrations of sucrose solution, embedded in OCT medium, and frozen on dry ice, followed by liquid nitrogen freezing.

For histopathological evaluation, 6-8 µm frozen or paraffin-embedded sections are stained with hematoxylin-eosin (H&E). IHC for human proliferation marker Ki-67 (clone MIB-1, IgG1, Immunotech, Westbrook, Me.) and other markers is performed on serial sections using an avidin-biotin-peroxidase system kit (Vector Laboratories, Burlingame, Calif.) and 3,3'-diaminobenzidine tetrahydrochloride (Sigma) as chromogen. Antigens are retrieved by microwave heat treatment in citrate buffer (BioGenex, San Ramon, Calif.). Prior to incubation with the positive control mouse antibody to human Ki-67 in a humidified chamber at room temperature for 1-2 hr, non-specific binding is blocked with 10% normal horse serum. Isotype-matched antibody is used as negative control for each staining.

Between each incubation step, slides are rinsed twice in PBS for 3-5 min. Biotin-labeled horse anti-mouse secondary antibody is applied for 30 min at room temperature, followed by incubation with a preformed avidin-biotinylated enzyme complex for 30 min. After color development by addition of the chromogen and counterstaining with Mayer's hematoxylin, sections are mounted and evaluated under a light microscope. Cultured, pelleted CTL, melanoma cells, or fibroblasts are used as positive control cells, which are fixed or frozen according to preparation of the reconstruct tissues.

Blocking antibodies are used for function analyses at a concentration of 10 and 2 µg/ml as described in (Somasundarum et al., 2000). Alternatively, viral chemokine and chemokine receptor homologs are used as described in (Biragyn & Kwak, 2000; Staib et al., 2001; Juhasz et al., 1993).

EXAMPLE 8

Comparison of CTL Activity in Reconstructs and in MLTC

CTL induction with fresh tissues in reconstruct and isolation of CTL (and melanoma cells) from reconstruct followed by propagation of CTL in MLTC. Fresh lymphocyte-rich tumor involved lymph node or cutaneous metastases specimens obtained within 3 hr of surgery are minced in cold RPMI 1640 (GIBCO) medium containing 100 IU of PennStrep (GIBCO). Finely minced tissues (1 mm³) are mixed with 250 µl of collagen and layered on freshly gelled fibroblast-collagen matrix. Cultures are submerged in reconstruct medium supplemented with complement-deactivated 10% human AB serum for 5-6 days. On day 7, reconstruct medium is replaced by T cell medium (RPMI 1640+5% IL-2+ 10% human AB serum). On day 14, if there are no or too few tumor cells in the reconstruct cultures, T cells are re-stimulated with freshly defrosted, irradiated tumor tissues (1 mm³) using fresh T cell medium. If tumor cells are growing in culture on day 14, T cells are cultured only with T cell medium. On day 21, cells are microdissected or isolated using antibody-coated beads, and analyzed by FACS using specific antibodies.

To further expand the already antigen-committed CTL, collagen supernatant containing T cells and a few non-adherent melanoma cells is collected by separating it from plastic-adherent melanoma cells and cultured in plastic wells for 4 weeks with periodic stimulation of tumor cells (derived from the adherent cells) and IL 2. To obtain sufficient number of cells for specificity and HLA restriction analyses, T cells are periodically stimulated with autologous tumor cells, EBV-B cells as APC and IL-2.T cells are phenotyped and characterized for their cytotoxic activity against fresh (cryopreserved and defrosted) melanoma cells, melanoma cells derived from the reconstruct, and cells derived from melanoma cell lines established outside the reconstruct using neutral red dye assay (Somasundarum et al., 2000).

EXAMPLE 9

Cloning of Selected Antigens Recognized by CTL that are Highly Effective in a Reconstruct Model HLA restriction element cloning. HLA restriction element cloning can be performed as described in (Somasundarum et al., 2000). Primers corresponding to the 5' and 3' end of the correct HLA gene are designed using the information available at the IMGT/HLA sequence data base (URL http file type, www host server, ebi.ac.uk domain name, imgt/hla/ directory). The primers are flanked by short sequences for restriction enzyme recognition. First strand cDNA is synthesized following standard protocols and used for PCR reaction with Roche's Expand High Fidelity PCR system. The use of the high fidelity PCR system reduces the risk of artificially introduced mutations during the PCR reaction. After cleavage of the DNA with the correct restriction enzymes and agarose gel purification, the PCR fragment is cloned into an expression plasmid such as pTracer™-CMV/BSD. This plasmid is useful, because the inserted GFP permits tracking of the transfection efficiency in COS cells. HLA mismatched tumor target cells are transfected with the HLA clone, and lysis of the transfected target cells by the CTL is evaluated to test for the distribution of the antigen.

Tumor cell expression cDNA library construction and antigen cloning. Total RNA is isolated from tumor cells, and full length cDNAs are synthesized using the SMART™ PCR cDNA synthesis kit, which allows high efficiency full length cDNA synthesis. After completion of the second strand synthesis, the DNA is polished and an adapter is attached. After adapter ligation and purification, the DNA is phosphorylated using kinase. An expression plasmid (e.g. pcDNA3.1) is cut with the correct restriction enzyme and dephosphorylated. Vector DNA and cDNA are combined and ligated. The ligated DNA is transfected into a host cell (e.g., *E. coli*). Electroporation is preferred, although other transfection methods, such as the $CaCl_2$ method, can be used. Alternatively, the cDNAs can be cloned into an expression phagemid (phagemid packaging and infection is more efficient than electroporation).

Twenty random clones are sequenced to determine the quality and diversity of the library. Typically, approximately 250,000 independent clones are screened to find low abundance genes with 99% probability (Maniatis et al., 1989; Ausubel et al., 1993). Therefore the initial library size preferably is at least $5 \times 10^5$ independent clones. Cells, such as COS-7 cells ($10^4$ per microtiter well), are co-transfected with the HLA plasmid and the miniprep cDNA pools of 100 cDNA clones using FuGene6 (Roche). Forty to 48 hr later the same number of T cells are added to each well and incubated for 48 hr. Supernatants are be tested in cytokine release assay (Somasundarum et al., 2000). Wells with at least 3 times the signal of control wells are considered positive. The cDNA of putative positive wells is tested again in triplicate. Positive pools are subcloned until a single CTL-reactive cDNA clone is isolated. The clone is sequenced, and the sequence is compared with all available databases, predominantly GenBank (URL http file type, www host server, ncbi.nlm.nih.gov domain name, Genbank/GenbankSearch.html directory). Computer prediction analysis can be used to help identify the CTL epitope, based on the HLA restriction element (see URL http file type, wehih.wehi.edu.au domain name, mhcpep/directory and URL http file type, www host server, brown.edu domain name, Research/TB-HIV_Lab/epimatrix.html directory).

Antigen characterization. The cDNA clone is transfected into autologous fibroblasts or EBV-B cells, and lysis of the transfected cells by the CTL is demonstrated to confirm the correct identity of the cDNA clone. The tissue distribution of the antigen can be determined by Northern blot analysis.

EXAMPLE 10

Characteristics of CTL007 and CTL007-F7 in MLTC and Reconstruct

CTL line 007 was established from patient 007 with rectal carcinoma stage Dukes' B by stimulating PBMC with autologous CRC cells WC007, using IL-2 from day 7 on. CTL expressed CD3, CD4, CD25, HLA-DR, and TCRα/β, but not CD40 and CD40 ligand. CTL produced IL-2, IL-4, IL-10, IFN-γ, and TNF-α. Analysis of the cytotoxic activity of the CTL line revealed lysis of autologous WC007 tumor cells in standard 4-6 h $^{51}$Cr-release assays at E:T ratios as low as 10 (minimum E:T ratio of 10 to cause significant tumor lysis of 12%; maximum lysis of 72% at E:T ratio of 50). Lysis of WC007 tumor cells was significant throughout the 23 wk culture period of the CTL line, and lytic activity was significantly enhanced by treatment of the tumor cells with IFN-γ. The CTL line also lysed allogeneic CRC cells HT-29, matched for HLA-A1 and WC016, matched for HLA-A3. Ag-specific lysis of WC007 CRC cells by the CTL line was significantly (p<0.05) inhibited by saturating concentrations of MAb W6/32 to HLA-class I, -A3, -DR, CD3, and CD4. Thus, lytic capacity of the uncloned CTL line is both HLA-class I (A1 and A3)- and HLA-class II (DR)-dependent, and both CD3 and CD4 of the CTL are involved.

WC007 tumor cells were destroyed by CTL007 in the rectal carcinoma reconstruct at an E:T ratio of 1. This ratio is ineffective in MLTC. Importantly, CTL were lytic in the reconstruct without the addition of exogenous IL-2, whereas IL-2 was essential in MLTC. CTL migrated from the fibroblast/collagen layer into the tumor cell/collagen/fibroblast layer which was placed on top of the CTL layer. In control cultures with PHA blasts, there was no significant lysis of tumor cells. Table 5 shows that statistically significant lower total number of tumor cells and higher number of apoptotic tumor cells (determined microscopically) are found in reconstructs containing CTL versus reconstructs containing PHA blast controls.

TABLE 5

Tumor-specific CTL007 decrease tumor cell growth and increase the number of apoptotic cells in a rectal carcinoma reconstruct

| Lymphocyte | Total no. tumor cells (mean +/− SD/5 fields) | % of apoptotic cells (mean +/− SD/5 fields) |
|---|---|---|
| CTL 007 | 41.2 +/− 7.04 | 11.8 +/− 4.3 |
| PHA blast | 69.6 +/− 16.7 | 6.0 +/− 2.3 |
| P value[1] | 0.008 | 0.029 |

[1]Comparison of CTL 007 vs PHA blast values; Student's 2-sided t-test.

CTL007 F7 was established similarly to CTL007. The CTL show stable growth for >3 months in culture. They are CD3 (99%) and CD4 (98%) positive, but CD8 negative. They lyse the autologous tumor cells (minimum E:T of 50 for significant lysis of 23%), but not autologous EBV-B cells, and allogeneic Daudi and K562 cells (<3.5% lysis). CTL007 F7 lysed CRC WC007 cells in the reconstruct at E:T ratio of 5. This ratio is ineffective in MLTC. Similar to the CTL007 reconstruct, CTL007 F7 were lytic in the reconstruct in the absence of exogenous IL-2, whereas they were IL-2 dependent in MLTC. Control reconstructs with PHA blasts seemed to indicate crypt formation by the CRC cells and showed no evidence of tumor cell lysis. Control T cell blasts are derived by stimulating PBMC with T cell mitogen (1% v/v PHA-M, Gibco) for 72 hr followed by cultivation in IL-2 containing medium.

In a CTL reconstruct stained with anti-caspase antibody there was strong black staining indicative of apoptotic cell death, whereas the same reconstruct stained with isotype-matched control antibody showed no significant staining. PHA blast control reconstruct stained with anti-caspase antibody showed very little evidence of apoptotic cell death. Staining of CTL reconstruct for lymphocyte marker CD45 revealed specific (red) staining of lymphocytes that migrated into the tumor cell area. Control PHA blasts reconstructs showed fewer lymphocytes, most of them remaining outside the tumor area. Thus, CTL007 F7 was effective in the reconstruct at a lower E:T ratio that was ineffective in MLTC. Notably, the results are indicative of CTL migration into the tumor cell layer, which was placed underneath the CTL layer. In contrast, in the experiment with a different CTL (CTL007), the CTL migrated upwards into the tumor cell layer. Thus, T cells seem to be able to migrate in both directions.

Table 6 shows significant lower total number of tumor cells and higher number of apoptotic tumor cells in the CTL007 F7 reconstruct versus the PHA blast control reconstruct.

TABLE 6

Tumor specific CTL007 F7 decrease tumor cell growth and increase the number of apoptotic cells in the rectal carcinoma reconstruct

| Lymphocyte | Total number of tumor cells mean ± SD/field (8 fields) | % of apoptotic cells mean ± SD/field (8 fields) |
|---|---|---|
| CTL007 F7 | 65.8 ± 12.9 | 21.6 ± 2.4 |
| PHA blast | 106.6 ± 30.3 | 10.1 ± 3.2 |
| P value[1] | 0.003 | <0.001 |

[1]Comparison of CTL007 F7 versus PHA blast values; Student's 2-sided t-test.

EXAMPLE 11

Preparation of Reconstructs Containing Primary Melanoma Cells

Melanoma tissues are obtained within 6 hr after surgery. Tumors are washed in RPMI 1640 medium containing 300 IU/ml penicillin, 300 µg/ml streptomycin, 300 µg/ml amikacin, 50 µg/ml gentamycin, and 2.5 µg/ml fungizone, followed by washing in versene containing 100 µg/ml gentamycin (antibiotics from Gibco), and minced to obtain 0.5-1 mm$^3$ pieces. Reconstructs are prepared by mixing neutralized type I collagen (Organogenesis, Canton, Mass., final concentration: 0.8-1 mg/ml) in MEM (BioWhittaker, Walkersville, Md.) supplemented with 10% human AB serum (Gemini Bio-Products, Woodlands, Calif.), 1.66 mM L-glutamine, 0.2% NaHCO$_3$ with the tumor pieces. The collagen-tumor mixture is plated into wells of 24-well plates (Corning, 5-8 pieces/well/1 ml). After gel formation, 1 ml medium (tumor/T cell medium 1:1) is added followed by incubation at 37° C. T cell medium contains RPMI 1640 supplemented with 216 mg/l L-glutamine, 50 µg/ml gentamycin 10 mM HEPES, $5 \times 10^{-5}$ M 2-mercaptoethanol (Sigma), and 10% heat-inactivated human AB serum (Gemini Bio-Products, Woodlands, Calif.). After 5 days incubation, medium is supplemented with 2% human natural IL-2 (Advanced Biotechnologies, Columbia, Md.). The amount of IL-2 is gradually increased to 5% by week 3. If tumor cells start dying, T cells are isolated and placed into new reconstructs with defrosted tumor pieces for T cell restimulation.

T cells and tumor cells are isolated for characterization by FACS analysis using anti-CD3 and anti-Melan A antibody (124) coated Dyna beads (Dynal), respectively. For IHC analysis, reconstructs are fixed in 10% neutral-buffered formalin (Fisher Scientific, Pittsburgh, Pa.) for 4 hr at room temperature, stored in 70% ethanol at 4° C. and embedded in paraffin. For frozen sections, tissues are dehydrated in increasing concentrations of sucrose solution, embedded in OCT medium and frozen on dry ice, followed by liquid nitrogen freezing.

EXAMPLE 12

Isolation of CTL from Fresh CRC Tissues in MLTC

Fresh tumor specimen obtained within 6 hr of surgery is minced, washed 2× in cold RPMI 1640 medium containing antibiotics (penicillin [300 IU/ml], streptomycin [300 µg/ml], amikacin [300 µg/ml] and fungizone [2.5 µg/ml]). An aliquot of minced tumor tissue is frozen in freezing media (90% human AB serum+10% DMSO) for future restimulation of MLTC. Minced tumor tissues (0.5-1 mm$^3$ pieces) are cultured in RPMI 1640 supplemented with 10% human AB serum in 24 well tissue culture treated plates (Corning, Corning, N.Y.). On day 3, cultures are supplemented with 5% purified human IL-2 (Advanced Biotechnologies, Columbia, Md.). On day 7, culture medium is replaced by RPMI 1640 supplemented with 10% human AB serum and 5% human IL-2 (T cell medium). On day 14, cultures with growing T cells are transferred into a new well and cultured in T cell medium. On day 21, T cell cultures are restimulated with irradiated frozen tumor tissues (3-4 0.5-1 mm$^3$ pieces/well). This procedure is repeated every 14 days or when growth of T cells slows down. Growing T cells are harvested, frozen in liquid N2 and further characterized. Wells with predominant adherent tumor cell monolayer growth are washed and supplemented with tumor cell media (MCDB201 medium containing 20% L15, 2% FBS, 10 mM glutamine, 0.05% NaHCO$_3$, 2 µg/ml insulin, 5 ng/ml EGF, 2 µg/ml transferrin). Culture medium is replaced by fresh tumor cell medium every 7 days. Growing tumor cells are further characterized as we have previously described in detail (Jacob et al., 1997).

EXAMPLE 13

Characterization of CTL Phenotype and Function

A $^{51}$Cr-release assay is used to determine tumor cell lysis by the CTL. If fresh (frozen and defrosted) tumor cells show high $^{51}$Cr release, the neutral red dye exclusion assay is used (Somasundarum et al., 2000). The minimal E:T ratio needed for tumor cell lysis by the CTL derived from the reconstruct or MLTC can be compared.

For IHC evaluation of the reconstructs, 6-8 µm frozen or paraffin-embedded sections are stained with H&E. IHC for

TABLE 7

| Patient No. | Established cell lines | | | Reconstruct/ MLTC | No. vials each with ~2 × 10$^6$ cryopreserved lymphocytes | | Phenotype (MLTC) |
|---|---|---|---|---|---|---|---|
| | Tumor | Fibroblasts | EBV-B | | MLTC | Reconstruct | |
| 3406 | + | + | + | both | 5 | 0 | CD4/CD8 |
| 3407 | + | + | + | MLTC | 2 | 0 | CD4/CD8 |
| 3408 | + | + | + | MLTC | 2 | 0 | CD4/CD8 |
| 3409 | − | − | + | both | 1 | 0 | CD4 |
| 3413 | − | − | + | both | 5 | 0 | CD4 |
| 3443 | + | − | + | both | 0 | 0 | not tested |
| 3445 | + | − | + | both | 5 | 0 | not tested |
| 3450 | + | − | + | both | 8 | 1 | not tested |
| 3451 | + | − | + | both | 9 | 6 | not tested |
| 3453 | + | + | + | both | 3 | 1 | not tested |
| 3454 | − | + | − | both | 2 | 8 | not tested |
| 3456 | − | + | + | both | 1 | 1 | not tested |
| 3457 | − | + | + | both | 0 | 0 | not tested |
| 3458 | + | − | − | both | 0 | 0 | not tested |
| 3461 | − | − | − | both | 0 | 0 | not tested |
| 3463 | − | − | − | both | 0 | 0 | not tested | human proliferation marker Ki-67 (clone MIB-1, IgG1, Immunotech, Westbrook, Me.), T cell markers CD4, CD8 and CD45, and tumor cell marker Melan-A or GA733 (45) is performed on serial sections using an avidin-biotin-peroxidase system kit (Vector Laboratories, Burlingame, Calif.) and 3,3'-diaminobenzidine tetrahydrochloride (Sigma) as chromogen. Ki-67 Ag is retrieved by microwave heat treatment in citrate buffer (BioGenex, San Ramon, Calif.). Non-specific binding is blocked with 10% normal horse serum before incubation with the mouse antibodies to these markers in a humidified chamber at room temperature for 1-2 hr. Isotype-matched murine anti-influenza virus antibody is used as negative control for each staining. Between each incubation step, slides are rinsed twice in PBS for 3-5 min.

Biotin-labeled horse anti-mouse secondary antibody is applied for 30 min at room temperature, followed by incubation with a preformed avidin-biotinylated enzyme complex for 30 min. After color development by addition of the chromogen and counterstaining with Mayer's hematoxylin, sections are mounted and evaluated under a light microscope. Cultured, pelleted T cells (PHA blasts), CRC cells, or fibroblasts are used as positive control cell lines, which will be fixed or frozen according to preparation of the reconstruct tissues. Lymph nodes (T cells), skin (fibroblasts), and CRC tissues are used as positive control tissues. An In Situ Cell Death Detection kit (TUNEL assay, Roche Molecular Biochemicals, Mannheim, Germany) is used for immunohistochemical detection and quantification of apoptosis at single cell level. Alternatively, sections can be stained with purified rabbit anti-human caspase 3 antibody specific for the active form of the enzyme (R&D Systems, Minneapolis, Minn.) after blocking sections with avidin-, biotin-, and protein-blocking agents (from Vector Laboratories, and Coulter-Immunotech) and rabbit antibody.

EXAMPLE 14

In Vitro Identification of Chemokines that Affect Active Migration of CTL Towards CRC Cells In Vivo CRC reconstructs with isolated CRC and CTL. A collagen-fibroblast layer is prepared by mixing neutralized type I collagen (Organogenesis, Canton, Mass., final concentration: 0.8-1 mg/ml) in MEM supplemented with 10% FBS, 1.66 mM L-glutamine, 0.2% $NaHCO_3$ with allogeneic human fetal colon fibroblasts (between passages 5-8, $1.8\times10^5$/well, $5\times10^5$/ml). Allogeneic fibroblasts will not provide alloantigenic stimulant to already committed CTL. Four-hundred fifty µl of the mixture is plated into wells of 24-well plates (Falcon, Becton Dickinson, Franklin Lakes, N.J.). After gel formation, 1 ml DMEM supplemented with 10% FBS and 50 µg/ml gentamycin is added, followed by incubation at 37° C. One day later, the medium is removed, and $10^5$ tumor cells are added on top of the first layer in 20 µl of medium. Tumor cells are allowed to attach for 2 hr at 37° C., followed by adding 1 ml medium (50% DMEM, 50% tumor cell medium—MCDB 201 containing 20% L-15, 2% FCS, 10 mM L-glutamine, 0.057% $NaHCO_3$, 2 µg/ml insulin, 5 ng/ml EGF, 2 µg/ml transferring. To provide a barrier between tumor cells and CTL, a fibroblast-collagen overlay is added for 24 hr.

The following day, a fibroblast-collagen overlay containing tumor-specific CTL pre-incubated with a chemokine-specific antibody is prepared by mixing $4\times10^5$/ml fibroblasts and $5\times10^5$/well CTL with collagen matrix, and 250 µl of the mixture are added/well. CTL incubated with an isotype-matched control antibody are used in control reconstructs. Cultures are incubated in medium (⅓ DMEM, ⅓ tumor cell medium, ⅓ T cell medium containing RPMI 1640 supplemented with 216 mg/L L-glutamine, 50 µg/ml gentamycin, 10 mM HEPES (Sigma), $5\times10^{-5}$ M 2-mercaptoethanol, and 10% heat-inactivated human AB serum) for four days.

Apoptotic cells are detected by in situ 3'-end-labeling of apoptotic fragmented DNA. An In Situ Cell Death Detection kit (TUNEL assay, Roche Molecular Biochemicals, Mannheim, Germany) can be used for immunohistochemical detection and quantification of apoptosis at single cell level. In another embodiment, apoptotic nuclei are detected microscopically. Briefly, after rehydration, sections can be first digested with 1.25 µg/ml Proteinase-K for 30 minutes at 40° C. Sections are rinsed in 70%, 90%, and 95% ethyl alcohol and air-dried at room temperature, followed by incubation with a nucleotide-DNA polymerase cocktail containing biotin-labeled dCTP and dATP, and non-labeled dTTP, dGTP at a concentration of 0.01 mM, and 5 units/ml Klenow fragment of DNA polymerase I (Invitrogen). A brown color can be developed using the streptavidin-biotin complex (ABC) and 3-3' diaminobenzidine substrate from Vector Laboratories. Sections can be counterstained with hematoxylin. The amount of tumor cell apoptosis can be compared between blocked and unblocked reconstructs using a two-sample t-test. If tumor cell apoptosis is greater in the control reconstruct, the chemokine is identified as involved in active CTL migration toward the tumor cells.

EXAMPLE 15

CTL Derived from the PBMC of a Colon Carcinoma Patient

PBMC from patient 013 (Dukes' stage C) were stimulated with irradiated autologous, long-term cultured tumor cells in the presence of irradiated autologous EBV-B cells. IL-2 (20 U/ml) was added to the cultures staring from the second week on. Stable CTL lines—C3 (CD8), D1 (CD4), E12 (CD8), A6 (CD4), F12 (CD8), and H7 (CD4)—were isolated that significantly lysed WC013 tumor cells (maximum lysis between 20 and >100% at E:T between 12.5 and 50). No lysis of LAK or NK specific targets (Daudi cells or K562 cells, respectively) was observed. Four of the 5 CTL lines tested for IFN-γ production produced significant amounts of the cytokine. Lysis of WC013 tumor cells by CTL E12 was HLA class I restricted and lysis of CTL A6 was both HLA class I and II restricted.

EXAMPLE 16

Expression of TCR Vα Chains in CTLs of Reconstructs Containing Melanoma Cells

TCR analysis of lymphocytes was performed in uncultured melanoma tissue, cells of MLTC, and reconstructs derived from patient 3451. Reconstructs were initiated by seeding minced tissue into bovine type I collagen in MEM supplemented with 10% human AB serum. Seven days later and then weekly, cultures received RPMI 1640 supplemented with 10% human AB serum and 10% natural IL-2.

MLTC were initiated by seeding minced tissues in RPMI 1640 medium supplemented with 10% human AB serum into plastic culture dishes. Seven days later and then weekly, cultures received 10% natural IL-2-containing medium (RPMI 1640 plus 10% human AB serum).

Vα chains 1, 3, 5, and 10 were found in MLTC cultures. Vα chains 3 and 7 were found in defrosted, uncultured tissue. Vα chain 10 was found in defrosted tissue cultured overnight. Vα chains 6, 7, 8, and 10 were found in PHA blasts from defrosted tissue after 3 weeks in culture.

The TCR of T lymphocytes isolated from reconstructs are more closely related to the TCR in situ than the TCR of T lymphocytes derived from MLTC. Moreover, the TCR repertoire is much greater in T cells derived from MLTC compared to those in a reconstruct, which suggests that considerable TCR skewing occurs in MLTC. Similar TCR skewing occurred after prolonged culture of the tissue in PHA.

EXAMPLE 17

Expression of TCR Vα Chains in Reconstructs Containing Colorectal Carcinoma Cells Colorectal carcinoma tissues were cultured as described in the example above. Vα chains 2, 6, 7, 8, 11, 13, 18, and 21 were found in the reconstructs. Vα chains 2, 3, 5, 6, 7, 11, and 12 were found in uncultured tissue. Vα chains 7, 12, 13, 17, and 21 were found in MLTC cultures.

As with the melanoma reconstructs described above, the TCR repertoire of the T lymphocytes derived from reconstructs were more similar to the repertoire of the lymphocytes in situ than the TCR repertoire of MLTC lymphocytes.

EXAMPLE 18

CTL Migration Through Additional Collagen Layer and Tumor Cell Apoptosis

Collagen and fibroblasts were seeded on the bottom of a well. A tumor cell layer was seeded on top of the bottom layer. A collagen fibroblast layer was seeded on top of this layer, followed by a very top layer of collagen, fibroblasts and T cells. Thus, T cells have to migrate through a collagen layer to reach tumor cells. The CTL killed the tumor cells as determined by apoptotic cell counts of H&E stained sections under the microscope. The counts were performed by two different observers. The apoptosis was significantly higher in CTL cultures than in control cultures (no T cells or PHA blasts) ($p<0.05$, student's t test). See Table 8.

Clark, W. H., Jr., Elder, D. E., Guerry, D., IV, Braitman, L. E., Trock, B. J., Schultz, D., Synnestvedt, M., and Halper, A. C. 1989. Model predicting survival in stage I melanoma based on tumor progression. J. Natl. Cancer Inst. 81: 1893-1894.

Lee, P. P., Yee, C., Savage, P. A., Fong, L., Brockstedt, D., Weber, J. S., Johnson, D., Swetter, S., Thompson, J., Greenberg, P. D., Roederer, M., and Davis, M. M. 1999b. Characterization of circulating T cells specific for tumor-associated antigen in melanoma patients. Nat. Med. 6: 677-685.

Finke, J., Ferrone, S., Frey, A., Mufson, A., and Ochoa, A. 1999. Where have all the T cells gone? Mechanisms of immune evasion by tumors. Immunol. Today 20: 158-160.

Nielsen, M.-B. and Marincola, F. M. 2000. Melanoma vaccines: the paradox of T cell activation without clinical response. Cancer Chemother. Pharmacol. 46: S62-S66.

Maaser, K., Wolf, K., Klein, C. E., Niggemann, B., Zänker, K. S., Bröcker, E.-B., and Friedl, P. 1999. Functional hierarchy of simultaneously expressed adhesion receptors: integrin alpha2beta1 but not CD44 mediated MV3 melanoma cell migration and matrix reorganization within three-dimensional hyaluronan-containing matrices. Mol. Biol. Cell 10: 3067-3079.

Friedl, P., Entschladen, F., Conrad, C., Niggemann, B., and Zänker, K. S. 1998. CD4+ T lymphocytes migrating in three-dimensional collagen lattices lack focal adhesions and utilize β1 integrin-independent strategies for polarization, interaction with collagen fibers and locomotion. Eur. J. Immunol. 28: 2331-2343.

Rao, W. H., Hales, J. M., and Camp, R. D. R. 2000. Potent costimulation of effector T lymphocytes by human collagen type I. J. Immunol. 165: 4935-4940.

Crowston, J. G., Salmon, M., Khaw, P. T., and Akbar, A. N. 1997. T-lymphocyte-fibroblast interactions. Biochem. Soc. Trans. 25: 529-531.

TABLE 8

Apoptotic tumor cells in reconstructs with CTL007

| Reconstruct | | | | | % of | Significance | | |
|---|---|---|---|---|---|---|---|---|
| | | | | | | (p value) of % values to | | |
| Tumor cells | T cells | Separating layer | Apoptotic cells +/− SD | Total cell number +/− SD | apoptotic cells +/− SD | No T cells | CTL | PHA blast |
| | | | Observer #1 | | | | | |
| WC007 | — | 100 ul | 7.1 +/− 2.8 | 90.1 +/− 26.3 | 8.19 +/− 3.5 | | + | +0.003 |
| WC007 | CTLoo7 | 100 ul | 23.5 +/− 8.7 | 80.5 +/− 38.8 | 31.7 +/− 11 | +<0.0001 | | +<0.0001 |
| WC007 | PHA bl | 100 ul | 15.9 +/− 6.8 | 136.2 +/− 54.8 | 12.1 +/− 3.9 | + | + | |
| | | | Observer #2 | | | | | |
| WC007 | — | 100 ul | 11.3 +/− 3.1 | 90.8 +/− 10.6 | 12.6 +/− 4.1 | | + | −0.165 |
| WC007 | CTLoo7 | 100 ul | 33.3 +/− 6.8 | 88.7 +/− 11.9 | 37.5 +/− 6.7 | +<0.0001 | | +<0.0001 |
| WC007 | PHAbl | 100 ul | 16.5 +/− 6.2 | 104.8 +/− 13.3 | 14.5 +/− 4.4 | − | + | |

REFERENCES

Lee, K.-H., Wang, E., Nielsen, M.-B., Wunderlich, J., Migueles, S., Connors, M., Steinberg, S. M., Rosenberg, S. A., and Marincola, F. M. 1999a. Increased vaccine-specific T cell frequency after peptide-based vaccination correlates with increased susceptibility to in vitro stimulation but does not lead to tumor regression. J. Immunol. 163: 6292-6300.

Schroder, J. M. 1995. Cytokine networks in skin. J. Invest. Dermatol. 105: 20S-24S.

Luger, T. A. and Schwarz, T. 1990. Evidence for an epidermal cytokine networks J. Invest. Dermatol. 95: 100S-104S.

Murakami, S. and Okada, H. 1997. Lymphocyte-fibroblast interactions. Crit. Rev. Oral Biol. Med. 8: 40-50.

Somasundaram, R., Robbins, P., Moonka, D., Loh, E., Marincola, F., Patel, A., Guerry, D., and Herlyn, D. 2000. CD4+, HLA class I-restricted, cytolytic T-lymphocyte clone against primary malignant melanoma cells. Int J. Cancer 85: 253-259.

Jacobs, N., Moutschen, M. P., Franzen-Detrooz, E., Boniver, V., Boniver, J., and Delvenne, P. 1998. Organotypic culture of HPV-transformed keratinocytes: a model for testing lymphocyte infiltration of (pre)neoplastic lesions of the uterine cervix. Virchows Arch 432: 323-330.

Jakic-Razumovic, J., Sale, G. E., Beauchamp, M. D., Storb, R., and Sandmaier, B. M. 1995. $CD8^+$ activated T lymphocytes produce an in vitro skin graft-versus-host reaction in an organotypic skin culture model. Transplantation 59: 69-78.

Gunzer, M., Schälfer, A., Borgmann, S., Grabbe, S., Zänker, K. S., Bröcker, E.-B., Kämpgen, E., and Friedl, P. 2000. Antigen presentation in extracellular matrix: interactions of T cells with dendritic cells are dynamic, short lived, and sequential. Immunity 13: 323-332.

Biragyn, A. and Kwak, L. W. 2000. Designer cancer vaccines are still in fashion. Nature Med. 6: 966-968.

Herlyn, D., Wettendorff, M., Schmoll, E., Iliopoulos, D., Schedel, I., Dreikhausen, U., Raab, R., Ross, A. h., jaksche, H., Scriba, M., and Koprowski, H. 1987. Anti-idiotype immunization of cancer patients: modulation of the immune response. Proc. Natl. Acad. Sci. USA 84: 8055-8059.

Staib, L., Birebent, B., Somasundaram, R., Purev, E., Braumüller, H., Leeser, C., Küttner, N., Li, W., Zhu, D., Wunner, W., Speicher, D., Beger, H-G., Song, H., Diao, J., and Herlyn, D. 2001. Immunogenicity of recombinant GA733-2E Ag (CO17-1A, EGP, KS1-4, KSA, Ep-CAM) in gastrointestinal carcinoma patients. Int. J. Cancer, in press.

Juhasz, I., Albelda, S. M., Elder, D. E., Murphy, G. F., Adachi, K., Herlyn, D., Valyi-Nagy, I., and Herlyn, M. 1993. Growth and invasion of human melanomas in human skin grafted to immunodeficient mice. Am. J. Pathol. 143: 528-537.

Hsu, M.-Y., Elder, D. E., and Herlyn, M. 1999. Melanoma: The Wistar Institute (WM) cell lines. In: Human Cell Culture (Mas Maniatis, T., Fritsch, E. F., and Sambrook, J. 1989. Molecular cloning: A laboratory manual. Cold Spring Harbor Laboratory.

Jacob, L., Somasundaram, R., Smith, W., Monos, D., Basak, S., Marincola, F., Pereira, S., and Herlyn, D. 1997. Cytotoxic T-cell clone against rectal carcinoma induced by stimulation of patient's peripheral blood mononuclear cells with autologous cultured tumor cells. Int. J. Cancer 71: 325-332.

Townsend, A. R., Rothbard, J., Gotch, F. M., Bahadur, G., Wraith, D., and McMichael, A. J. 1986. The eoptopes of influenza nucleoprotein recognized by cytotoxic T lymphocytes can be defined with short synthetic peptides. Cell 44: 959-968.

Yasukawa, M., Inatsuki, A., and Kobayashi, Y. 1989. Differential in vitro activation of $CD4^+CD8$ and $CD8^+CD4$. Herpes simplex virus-specific human cytotoxic T cells. J. Immunol. 143: 2051-2057.

Hayashi, Y., Hoon, D. S. B., Park, M. S., Terasaki, P. I., Foshag, L. J., and Morton, D. L. 1992. Induction of $CD4^+$ cytotoxic T cells by sensitization with allogeneic melanomas bearing shared or cross-reactive HLA-A. Cell. Immunol. 139: 411-425.

Go, C., Lancid, D. W., Fitch, F. W., and Miller, J. 1993. Anergized T cell clones retain their cytolytic ability. J. Immunol. 150: 367-376.

Barnd, D. L., Lan, M. S., Metzgar, R. S., and Finn. O. J. 1989. Specific, major histocompatibility complex-unrestricted recognition of tumor-associated mucins by human cytotoxic T cells. Proc. Natl. Acad. Sci. USA 86: 7159-7163.

Ausubel, F. M., Brent, R., Kingston, R. E., Moore, D. D., Seidman, J. G., Smith, J. A., and Struhl, K. 1993. Current protocols in molecular biology.

Jacob, L., Somasundaram, R., Smith, W., Monos, D., Basak, S., Marincola, F., Pereira, S., and Herlyn, D. 1997. Cytotoxic T cell clone against rectal carcinoma induced by stimulation of a patient's peripheral blood mononuclear cells with autologous cultured tumor cells. Int. J. Cancer 71: 325-332.

Weber, Peptide Vaccines for Cancer, *Cancer Investigation* 20, 208-221, 2002

Homey et al., Chemokines: Agents for the Immunotherapy of Cancer? *Nature Rev.* 2, 175, 2002

The invention claimed is:

1. A non-naturally occurring model for detecting active migration of cells, comprising:
   (a) a first solid layer comprising collagen and fibroblasts;
   (b) a cellular layer in contact with the first solid layer and comprising a first cell type;
   (c) a second solid layer covering the cellular layer and comprising collagen and fibroblasts; and
   (d) a third solid layer in contact with the second solid layer and comprising collagen, fibroblasts, and a second cell type, wherein the second cell type is a migratory cell.

2. A non-naturally occurring model for detecting active migration of cytotoxic T lymphocytes, comprising:
   (a) a first solid layer comprising collagen and fibroblasts;
   (b) a cellular layer in contact with the first solid layer and comprising tumor cells;
   (c) a second solid layer covering the cellular layer and comprising collagen and fibroblasts; and
   (d) a third solid layer in contact with the second solid layer and comprising collagen, fibroblasts, and cytotoxic T lymphocytes.

3. A method of detecting active migration of migratory cells, comprising the steps of:
   (a) detecting at a first time first positions migratory cells in the third solid layer of the composition of claim 1; and
   (b) detecting at a second time second positions of the migratory cells, wherein a difference in the first and second positions indicates active migration of the migratory cells.

4. A method of detecting active migration of cytotoxic T lymphocytes, comprising the steps of:
   (a) detecting at a first time first positions of cytotoxic T lymphocytes in the third solid layer of the composition of claim 2; and
   (b) detecting at a second time second positions of the cytotoxic T lymphocytes, wherein a difference in the first and second positions indicates active migration of the migratory cells.

5. A method of detecting active migration of cytotoxic T lymphocytes towards tumor cells, comprising the steps of:
   (a) detecting tumor cell lysis in a first composition comprising (1) a first solid layer comprising collagen and fibroblasts, (2) a cellular layer in contact with the first solid layer and comprising tumor cells, (3) a second solid layer covering the cellular layer and comprising collagen and fibroblasts, and (4) a third solid layer in contact with the second solid layer and comprising collagen, fibroblasts, and cytotoxic T lymphocytes; and
   (b) detecting tumor cell lysis in a second composition comprising (1) a first solid layer comprising collagen and fibroblasts, (2) a cellular layer in contact with the first solid layer and comprising tumor cells, (3) a second solid layer covering the cellular layer and comprising collagen and fibroblasts, and (4) a third solid layer in contact with the second solid layer and comprising collagen, fibroblasts, and control lymphocytes that are not cytotoxic T lymphocytes, wherein increased tumor cell lysis in the first composition compared with the second composition indicates active migration of the cytotoxic T lymphocytes towards the tumor cells in the first composition.

6. A method of detecting cytotoxicity of cytotoxic T lymphocytes, comprising the steps of:
    comparing a first percentage of killed tumor cells in a first composition comprising:
        (a) a first solid layer comprising collagen and fibroblasts;
        (b) a cellular layer in contact with the first solid layer and comprising tumor cells;
        (c) a second solid layer covering the cellular layer and comprising collagen and fibroblasts; and
        (d) a third solid layer in contact with the second solid layer and comprising collagen, fibroblasts, and cytotoxic T lymphocytes; with a second percentage of killed tumor cells in a second composition comprising:
        (a) a first solid layer comprising collagen and fibroblasts;
        (b) a cellular layer in contact with the first solid layer and comprising tumor cells;
        (c) a second solid layer covering the cellular layer and comprising collagen and fibroblasts; and
        (d) a third solid layer in contact with the second solid layer and comprising collagen, fibroblasts, and phytohemagglutinin-treated blast cells;
    wherein an increase between the first and the second percentages indicates cytotoxic T lymphocyte-induced killing of tumor cells in the first composition.

7. A method of identifying a tumor antigen that binds to a T cell receptor of a cytotoxic T lymphocyte that induces killing of tumor cells, comprising the steps of:
    (a) identifying a clone of cytotoxic T lymphocytes that induce killing of tumor cells by a method comprising the steps of:
        (1) comparing a first percentage of killed tumor cells in a first composition comprising:
            (i) a first solid layer comprising collagen and fibroblasts;
            (ii) a cellular layer in contact with the first solid layer and comprising tumor cells;
            (iii) a second solid layer covering the cellular layer and comprising collagen and fibroblasts; and
            (iv) a third solid layer in contact with the second solid layer and comprising collagen, fibroblasts, and cytotoxic T lymphocytes;
        with a second percentage of killed tumor cells in a second composition comprising:
            (i) a first solid layer comprising collagen and fibroblasts;
            (ii) a cellular layer in contact with the first solid layer and comprising tumor cells;
            (iii) a second solid layer covering the cellular layer and comprising collagen and fibroblasts; and
            (iv) a third solid layer in contact with the second solid layer and comprising collagen, fibroblasts, and phytohemagglutinin-treated blast cells;
        wherein an increase between the first and the second percentages indicates cytotoxic T lymphocyte-induced killing of tumor cells in the first composition;
    (b) testing host cells that express an HLA restriction element autologous for the cytotoxic T lymphocytes identified in step (a) and comprising cDNA of the tumor cells to identify a host cell that induces cytokine release in cytotoxic T lymphocytes of the clone; and
    (c) isolating tumor cell cDNA from the host cell, wherein the tumor cell cDNA encodes a tumor-associated antigen.

8. A method of identifying a chemokine that influences active migration of migratory cells, comprising the steps of:
    (a) identifying a chemokine receptor expressed by a first population of migratory cells;
    (b) contacting the first population with an antibody that specifically binds to the chemokine receptor; and
    (c) comparing active migration of the first population with active migration of a second population of migratory cells that has not been contacted with the first molecule, wherein a difference in active migration between the first and second populations identifies a chemokine which binds to the chemokine receptor as influencing active migration of the migratory cells, and wherein active migration of the first and second populations is detected by a method comprising the steps of:
        (1) detecting at a first time first positions of migratory cells in a third solid layer of a composition comprising (i) a first solid layer comprising collagen and fibroblasts, (ii) a tumor cell layer in contact with the first solid layer, (iii) a second solid layer covering the tumor cell layer and comprising collagen and fibroblasts; and (iv) the third solid layer in contact with the second solid layer and comprising collagen, fibroblasts, and cytotoxic T lymphocytes; and
        (2) detecting at a second time second positions of the migratory cells, wherein a difference in the first and second positions indicates active migration of the migratory cells.

9. A method of identifying a chemokine or a cytokine that influences active migration of migratory cells, comprising the step of:
    comparing active migration of a first population of migratory cells with active migration of a second population of migratory cells, wherein a difference in active migration between the first and second populations identifies the chemokine or the cytokine as influencing active migration of the migratory cells, and wherein active migration of the first population is detected by a method comprising the steps of:
    (a) detecting at a first time first positions of the first population in a third solid layer of a first composition, wherein the first composition comprises (1) a first solid layer comprising collagen and fibroblasts, (2) a target cell layer in contact with the first solid layer, (3) a second solid layer covering the target cell layer and comprising collagen and fibroblasts; and (4) the third solid layer in contact with the second solid layer and comprising collagen, fibroblasts, and the first population, wherein the first composition further comprises an antibody that specifically binds to a chemokine or a cytokine; and
    (b) detecting at a second time second positions of the first population, wherein a difference in the first and second positions indicates active migration of the first population, and wherein active migration of the second population is detected by a method comprising the steps of:

(a) detecting at a first time first positions of the second population in a third solid layer of a second composition, wherein the second composition comprises (1) a first solid layer comprising collagen and fibroblasts, (2) a target cell layer in contact with the first solid layer, (3) a second solid layer covering the target cell layer and comprising collagen and fibroblasts; and (4) the third solid layer in contact with the second solid layer and comprising collagen, fibroblasts, and the second population; and (b) detecting at a second time second positions of the second population, wherein a difference in the first and second positions indicates active migration of the second population.

10. The model of claim 1 wherein the migratory cell is a leukocyte.

11. The model of claim 1 wherein the migratory cell is a lymphocyte.

12. The model of claim 1 wherein the migratory cell is a natural killer cell.

13. The model of claim 1 wherein the migratory cell is a T lymphocyte.

14. The model of claim 1 wherein the migratory cell is a cytotoxic T lymphocyte.

15. The model of claim 1 wherein the first cell type is a tumor cell.

16. The model of claim 1 wherein the first cell type is a colon tumor cell.

17. The model of claim 1 wherein the first cell type is a melanoma cell.

18. The method of claim 3 wherein the migratory cells are leukocytes.

19. The method of claim 3 wherein the migratory cells are lymphocytes.

20. The method of claim 3 wherein the migratory cells are natural killer cells.

21. The method of claim 3 wherein the migratory cells are T lymphocytes.

22. The method of claim 3 wherein the migratory cells are cytotoxic T lymphocytes.

23. The method of claim 3 wherein the first cell type is a tumor cell.

24. The method of claim 3 wherein the first cell type is a colon tumor cell.

25. The method of claim 3 wherein the first cell type is a melanoma cell.

26. The method of claim 5 wherein the control lymphocytes are phytohemagglutinin-treated blast cells.

27. The method of claim 4 wherein an antibody is specifically bound to a chemokine receptor on the cytotoxic T lymphocytes.

28. The method of claim 4 wherein the first and second compositions further comprise an antibody that specifically binds to a chemokine.

29. The method of claim 4 wherein the first and second compositions further comprise an antibody that specifically binds to a cytokine.

30. The method of claim 6 wherein the cytotoxic T lymphocytes migrate to the cellular layer.

31. The method of claim 6 wherein the cytotoxic T lymphocytes and the phytohemagglutinin-treated blasts cells are obtained from the same individual.

32. The method of claim 6 wherein the tumor cells are colon tumor cells.

33. The method of claim 6 wherein the tumor cells are melanoma cells.

34. The method of claim 7 wherein the cytotoxic T lymphocytes migrate to the cellular layer.

35. The method of claim 7 wherein the tumor cells are colon tumor cells.

36. The method of claim 7 wherein the tumor cells are melanoma cells.

37. The method of claim 8 wherein the migratory cells are leukocytes.

38. The method of claim 8 wherein the migratory cells are lymphocytes.

39. The method of claim 8 wherein the migratory cells are natural killer cells.

40. The method of claim 8 wherein the migratory cells are T lymphocytes.

41. The method of claim 8 wherein the migratory cells are cytotoxic T lymphocytes.

42. The method of claim 9 wherein the migratory cells are leukocytes.

43. The method of claim 9 wherein the migratory cells are lymphocytes.

44. The method of claim 9 wherein the migratory cells are natural killer cells.

45. The method of claim 9 wherein the migratory cells are T lymphocytes.

46. The method of claim 9 wherein the migratory cells are cytotoxic T lymphocytes.

47. The method of claim 5 wherein an antibody is specifically bound to a chemokine receptor on the cytotoxic T lymphocytes.

48. The method of claim 5 wherein the first and second compositions further comprise an antibody that specifically binds to a chemokine.

49. The method of claim 5 wherein the first and second compositions further comprise an antibody that specifically binds to a cytokine.

* * * * *